(12) United States Patent
Mayse et al.

(10) Patent No.: US 11,779,741 B1
(45) Date of Patent: Oct. 10, 2023

(54) FLUID-MANAGEMENT SYSTEM AND METHOD

(71) Applicant: Pleural Dynamics, Inc., Wayzata, MN (US)

(72) Inventors: Martin Mayse, Wayzata, MN (US); John Streeter, Redmond, WA (US)

(73) Assignee: Pleural Dynamics, Inc., Wayzata, MN (US)

( * ) Notice: Subject to any disclaimer, the term of this patent is extended or adjusted under 35 U.S.C. 154(b) by 0 days.

(21) Appl. No.: 18/103,773

(22) Filed: Jan. 31, 2023

Related U.S. Application Data

(63) Continuation of application No. 17/733,138, filed on Apr. 29, 2022, now Pat. No. 11,577,065.

(51) Int. Cl.
*A61M 39/24* (2006.01)
*A61M 39/02* (2006.01)

(52) U.S. Cl.
CPC ........ *A61M 39/0247* (2013.01); *A61M 39/24* (2013.01); *A61M 2039/0252* (2013.01); *A61M 2039/242* (2013.01); *A61M 2039/2426* (2013.01); *A61M 2210/101* (2013.01)

(58) Field of Classification Search
CPC .............. A61M 39/0247; A61M 39/24; A61M 2039/242; A61M 2039/2426; A61M 2210/101
See application file for complete search history.

(56) References Cited

U.S. PATENT DOCUMENTS

| | | | |
|---|---|---|---|
| 3,463,159 A | 8/1969 | Heimlich | |
| 5,009,635 A | 4/1991 | Scarberry | |
| 5,484,401 A | 1/1996 | Rodriguez et al. | |
| 5,738,656 A | 4/1998 | Wagner | |
| 6,254,581 B1 | 7/2001 | Scott | |
| 7,135,010 B2 | 11/2006 | Buckman et al. | |
| 7,326,197 B2 | 2/2008 | Breznock et al. | |
| 7,766,886 B2 | 8/2010 | Garcia et al. | |
| 8,518,053 B2 | 8/2013 | Tanaka et al. | |

(Continued)

FOREIGN PATENT DOCUMENTS

| | | |
|---|---|---|
| EP | 2714178 B1 | 12/2015 |
| WO | 2010026458 A1 | 3/2010 |

OTHER PUBLICATIONS

Aspira Drainage System, "Aspira Drainage System Product Features," 2 pages. [retrieved on Apr. 25, 2022], Retrieved from the Internet: URL: <https://www.myaspira.com/clinicians/aspira-product-features/>.

(Continued)

*Primary Examiner* — Deanna K Hall
(74) *Attorney, Agent, or Firm* — LEE SULLIVAN SHEA & SMITH LLP

(57) ABSTRACT

A fluid-management system for selectively draining fluid from a body cavity includes a valve assembly and a tube for carrying fluid from a body cavity of a person to the valve assembly. The valve assembly is configured to be positioned external to the person's body and comprises (i) an inlet, (ii) an outlet, (iii) one or more one-way valves positioned between the inlet and outlet that are each configured to open and close based on fluctuations in pressure between the person's body cavity and the one-way valve, and (iv) an adjustable outlet lock configured to selectively prevent fluid movement through the outlet.

19 Claims, 16 Drawing Sheets

(56) References Cited

U.S. PATENT DOCUMENTS

| | | | |
|---|---|---|---|
| 8,636,721 | B2 | 1/2014 | Alam et al. |
| 9,314,599 | B2 | 4/2016 | Karwoski et al. |
| 9,393,353 | B2 | 7/2016 | Alam et al. |
| 9,393,387 | B1 | 7/2016 | Mayse et al. |
| 9,907,887 | B2 | 3/2018 | Alam et al. |
| 10,213,532 | B2 | 2/2019 | Alam et al. |
| 10,265,442 | B2 | 4/2019 | Luxon et al. |
| 10,517,538 | B2 | 12/2019 | Burnett et al. |
| 10,646,629 | B2 | 5/2020 | Roe et al. |
| 10,905,815 | B2 | 2/2021 | Doshi et al. |
| 2007/0078442 | A1* | 4/2007 | Mayse .............. A61M 39/10 604/533 |
| 2008/0125750 | A1 | 5/2008 | Gaissert |
| 2019/0358438 | A1 | 11/2019 | Fortune et al. |
| 2021/0283330 | A1 | 9/2021 | Mayse |

OTHER PUBLICATIONS

Gogakos, Apostolos et al., "Heimlich valve and pneumothorax," Annals of Translational Medicine vol. 3(4), Mar. 2015, 7 pages. [retrieved on Apr. 25, 2022], Retrieved from the Internet: URL: <https://www.ncbi.nlm.nih.gov/pmc/articles/PMC4381465/>.

CareFusion Corporation, "Denver ascites shunts for patients with refractory ascites," 2012, 8 pages.

Bearpac Medical, "Passio Pump Drainage System," 2022, 2 pages. [retrieved on Apr. 25, 2022], Retrieved from the Internet: URL: <https://bearpac.com/passio-pump-drainage-system-2/>.

St. Joseph's Healthcare Hamilton, "A Heimlich Valve for Chest Drainage," Mar. 2005, 2 pages. [retrieved on Apr. 25, 2022], Retrieved from the Internet: URL: <https://bearpac.com/passio-pump-drainage-system-2/>.

Memorial Sloan Kettering Cancer Center, "About your PleurX Drainage Catheter," Jul. 12, 2021, 23 pages. [retrieved on Apr. 26, 2022], Retrieved from the Internet: URL: <https://www.mskcc.org/pdf/cancer-care/patient-education/about-your-pleurx-drainage-catheter>.

Potter, Perry, "Closed Chest Drainage Systems," 2014, Chapter 26, pp. 655-671, 17 pages. [retrieved on Apr. 26, 20226], Retrieved from the Internet: URL: <https://library.upei.ca/sites/library.upei.ca/files/Nurs2230X_PerryPotter_2014_655-671.pdf>.

Porcel, José M, "Chest Tube Drainage of the Pleural Space: A Concise Review for Pulmonologists," Tuberculosis and Respiratory Diseases vol. 81,2. Apr. 2018, 12 pages. [retrieved on Apr. 26, 2022], Retrieved from the Internet: URL: <https://www.ncbi.nlm.nih.gov/pmc/articles/PMC5874139/#>.

International Searching Authority, PCT International Search Report and Written Opinion, PCT International Application No. PCT/US2023/020231, dated Aug. 7, 2023, 11 pages.

\* cited by examiner

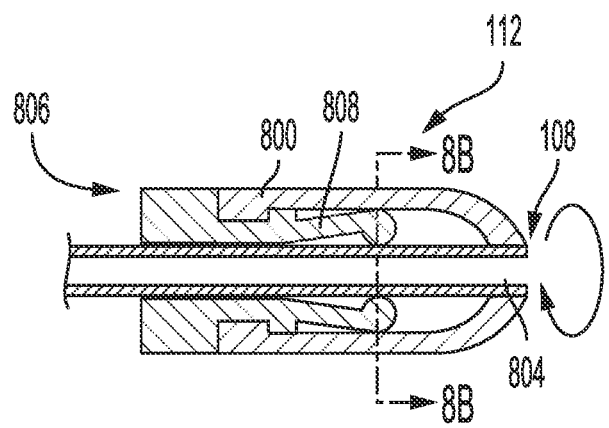
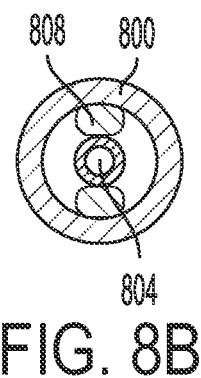
FIG. 8A  FIG. 8B
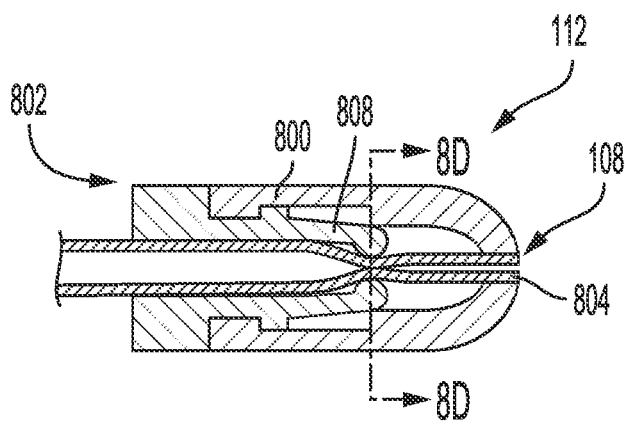
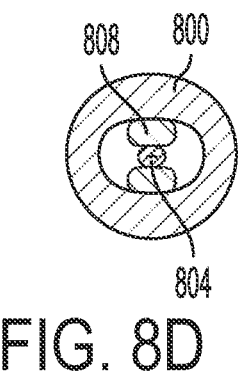
FIG. 8C  FIG. 8D

FLUID-MANAGEMENT SYSTEM AND METHOD

CROSS-REFERENCE TO RELATED APPLICATION

This application is a continuation of, and claims the benefit of priority under 35 U.S.C. § 120 to, U.S. application Ser. No. 17/733,138, filed on Apr. 29, 2022 and titled "Fluid-Management System and Method," the contents of which are incorporated herein by reference in its entirety.

BACKGROUND

A number of techniques for draining bodily fluid involve utilizing a pump, in combination with a tube (e.g., a shunt or catheter), to drain fluid from one cavity within the human body to either another cavity within the body or to a reservoir outside of the body. Such techniques may be utilized for purposes including, for example, draining a person's blood, urine, saliva, cerebrospinal fluid, peritoneal fluid, pleural fluid, and/or cystic-lesion fluid, among other possibilities.

OVERVIEW

When fluid builds up in a cavity of a person's body, it is often necessary to drain the fluid to either another cavity within the body or to outside of the body. Fluid may build up for one reason or another in various body cavities such as a pleural cavity, a peritoneal cavity, a cerebrospinal cavity, a breast cavity, a cavity of a cystic lesion in the body (e.g., a cystic lesion in the breast, a cystic lesion in the abdomen, etc.), a cavity left following surgery, among other possibilities.

In some situations, it may be desirable to drain fluid by moving the fluid (i) from a body cavity, (ii) through an implanted tube in fluid communication with the body cavity, and (iii) into an external reservoir located outside the person's body. Further, in some situations, it may also be desirable for a person to not have a permanently-attached external drainage reservoir attached to the implanted tube that is in fluid communication with the body cavity, but rather have the ability to intermittently drain the body cavity into an external drainage reservoir when convenient for the person. Such selective draining of fluid from the body cavity may, for instance, help a person drain fluid build-up before the fluid build-up becomes uncomfortable while also avoiding the need for a permanently-attached external drainage reservoir. Allowing a person to control when to selectively drain fluid and avoiding the need for a permanently-attached external drainage reservoir may provide a person greater freedom and flexibility compared to a situation in which a person is unable to selectively control when to drain fluid and/or has a permanently-attached external drainage reservoir.

One example situation in which it may be desirable to selectively drain fluid from a person's body cavity into an external drainage reservoir that is not permanently attached to the person is drainage of pleural fluid for the treatment of pleural effusions. Pleural fluid is normally a low-protein liquid that can be found in relatively small amounts (normally 10-20 milliliters) in each of a person's pleural cavities. The pleural cavities are the spaces between the visceral pleura (i.e., the membrane located over the entire outer surface of each lung) and the parietal pleura (i.e., the membrane lining the inside of the chest wall of each hemithorax). The small amount of pleural fluid in each pleural space is spread out very thinly between the visceral and parietal pleura thereby providing for a large surface tension which mechanically couples the lung to the chest wall while simultaneously lubricating these surfaces allowing the lung to slide over the chest wall during the breathing process. In a normal, healthy person, pleural fluid is constantly being produced—largely from leakage of fluid from blood and lymphatic vessels in the visceral pleura that coats the outer surface of the lung—and reabsorbed at essentially the same rate by lymphatic channels located in the parietal pleural that lines the chest wall. This dynamic balance exchanges the fluid multiple times a day and typically maintains a low total volume in the 10-20 milliliter range. However, under certain abnormal conditions, such as infection, inflammation, malignancy, heart failure, liver failure, or kidney failure, among other possible conditions, the net flow of pleural fluid within the pleural cavity becomes unbalanced, with increased fluid production and/or decreased reabsorption, resulting in the excess accumulation (e.g., on the order several hundred milliliters to several liters) of fluid in the pleural space.

Excess accumulation of pleural fluid is known as pleural effusion and adds additional mass that must be moved with each breath and may cause the pathological compression of lung tissue. This compression results in considerable difficulty in or prevention of the breathing process. Pleural effusion may lead to various issues, such as dyspnea, shortness of breath, chest pain, and/or chronic cough, among other possibilities, and may greatly compromise a person's quality of life. Draining of the excess accumulation of pleural fluid may help to alleviate, reduce or eliminate such issues. Treatment of a pleural effusion may involve draining of pleural fluid into either another body cavity or outside of the body, and in some situations, it may be desirable to treat a pleural effusion by selectively draining fluid from the pleural cavity into an external reservoir.

While there are certain fluid-management systems existing that allow a person to selectively control when to drain excess fluid from a body cavity (e.g., a pleural cavity) via an implanted tube such that an external reservoir is not always attached to the implanted tube, these existing fluid-management systems typically utilize a dedicated pump-and-reservoir assembly that can be removably attached to the implanted tube. The dedicated pump-and-reservoir assembly includes an active pumping component for pumping fluid out of the body cavity and a drainage reservoir for collecting the pumped fluid. The active pumping component serves to force fluid to move through the implanted tube and into the drainage reservoir. In an example, the active pumping component is a vacuum-based component that is configured to provide vacuum pressure to facilitate draining from the body cavity. For instance, in an example, a dedicated pump-and-reservoir assembly includes a vacuum bottle that, upon attachment to the implanted tube and activation of the vacuum (e.g., via breaking of a vacuum seal of the vacuum bottle), provides vacuum pressure to move fluid from the person's body cavity, through the implanted tube, and into the vacuum bottle.

When a person desires to drain the fluid within the body cavity using a dedicated pump-and-reservoir assembly, the person needs to (i) access the dedicated pump-and-reservoir assembly, (ii) sterilize both the component(s) of the dedicated pump-and-reservoir assembly to be connected to the implanted tube and the attachment point of the implanted tube, (iii) attach the dedicated pump-and-reservoir assembly to the implanted tube, and (iv) activate the active pumping component to facilitate draining of the body cavity. Further, after completing draining of the body cavity, the person then needs to detach the dedicated pump-and-reservoir assembly from the implanted tube, as well as decontaminate and sterilize the attachment point of the implanted tube. However, the existing fluid-management systems such as this that allow a person to selectively control when to drain excess fluid from a body cavity by utilizing a dedicated pump-and-reservoir assembly have numerous drawbacks.

One such drawback of existing fluid-management systems is that a person cannot drain fluid from the body cavity with the implanted tube unless the person has access to the dedicated pump-and-reservoir assembly. However, in practice, it is often difficult and/or inconvenient for a person to always bring with them a dedicated pump-and-reservoir assembly or otherwise ensure that they always have access to the dedicated pump-and-reservoir assembly when needed. For instance, the dedicated pump-and-reservoir assemblies can be bulky and/or difficult transport. Further, people may often forget to bring a dedicated pump-and-reservoir assembly with them (e.g., when leaving the person's house for one reason or another, the person may forget the dedicated pump-and-reservoir assembly and instead leave it at home). Therefore, with the existing fluid-management systems, a person may be unable to drain fluid from the body at the desired or needed time.

Another drawback of existing fluid-management systems is that the dedicated pump-and-reservoir assemblies may be costly and/or difficult for a person to obtain. For instance, the dedicated pump-and-reservoir assemblies may be single-use assemblies that are disposed of after draining, and these may be costly for persons using the assemblies and/or insurance companies for persons using the assemblies. Further, in some examples, the dedicated pump-and-reservoir assembly includes a reusable pumping component (e.g., a reusable motorized peristaltic pump) and a single-use dedicated drainage line and reservoir, and these may be costly for persons using the assemblies and/or insurance companies for persons using the assemblies. Such cost issues may make it difficult for a person to obtain the dedicated pump-and-reservoir assemblies. Further, it may be difficult for a person to always have a dedicated pump-and-reservoir assembly on hand and/or obtain a dedicated pump-and-reservoir assembly when needed. Such issues may in turn reduce compliance with a person's treatment plan (e.g., a doctor-specified draining schedule for draining the body cavity).

Yet another example drawback of existing fluid-management systems is that the process of connecting the dedicated pump-and-reservoir assembly to the implanted tube can be a cumbersome process.

Still yet another example drawback of existing fluid-management systems is that the task of connecting the components(s) of the dedicated pump-and-reservoir assembly to the attachment point of the implanted tube may be associated with a risk of contamination (e.g., if one or more of the components being attached is not sterile). Further, contamination may be associated with a risk of infection, and existing fluid-management systems have a reported infection rate of approximately 5-10%. In existing fluid-management systems, the reservoir and attachment line are typically single-use and provided sterile. The implanted tube to which the reservoir and attachment line are attached is typically decontaminated, for example, with an alcohol swab or betadine swab. The sterile, disposable, attachment line is then connected to this decontaminated portion of the implanted tube. In some existing fluid-management systems, the sterile part is passed through the decontaminate part and into the interior of the implanted tube that is in direct fluid communication with the pleural space. Infection may occur during use of existing fluid-management systems for various reasons, such as bacterial colonization of the implanted tube entry point and/or the distal access of the implanted tube itself. Further, in existing fluid management systems, when the implanted tube is accessed, the systems do not actively prevent retrograde flow (also referred to herein as "backflow") during the draining process, and backflow may be associated with a risk on contamination and/or infection.

To help address the aforementioned and other problems, disclosed herein is new fluid-management system for selectively draining fluid from a body cavity. The disclosed fluid-management system includes a valve assembly and a tube for carrying fluid from a body cavity of a person to the valve assembly. The valve assembly is configured to be positioned external to the person's body and comprises (i) an inlet, (ii) an outlet, (iii) one or more one-way valves positioned between the inlet and outlet that are each configured to open and close based on fluctuations in pressure between the person's body cavity and the one-way valve, and (iv) an adjustable outlet lock configured to selectively prevent fluid movement through the outlet. In some implementations, the one or more one-way valves of the valve assembly may take the form of a single one-way valve, while in other implementations, the one or more one-way valves of the valve assembly may take the form of two one-way valves arranged in series, among other possibilities. In implementations where the one or more one-way valves of the valve assembly take the form of two one-way valves arranged in series, the two one-way valves of the valve assembly may be arranged in series within a pumping chamber that is configured to allow a person to prime the fluid-management system. The tube may be configured to extend from the inlet of the valve assembly to the person's body cavity and allow movement of fluid from the person's body cavity to the inlet of the valve assembly. In this way, the fluid-management system may be selectively used by the person to drain fluid into any appropriate external reservoir, such as a sink, a commode, and/or a container provided by the person, among other possibilities.

As noted, the one or more one-way valves are each configured to open and close based on fluctuations in pressure between the body cavity and the one-way valve, which allows fluid movement out of the outlet and also prevents retrograde flow (also referred to herein as "backflow") in the fluid-management system (e.g., flow of liquid and/or air back into the tube). In practice, retrograde flow may result in aspiration of air back into the body cavity (e.g., a pleural cavity) or flow of liquid back into the cavity, and such retrograde flow could cause various issues such as infection by allowing bacterial entry and/or collapse of the lung. Therefore, preventing retrograde may help to avoid such issues that may be associated with flow of liquid and/or air back into the tube.

Additionally, the opening and closing of the one or more one-way valves may also provide a pumping action that helps move fluid from the cavity through the tube and the valve assembly. In this regard, in some examples, the fluctuations in pressure between the body cavity and the one or more one-way valves occur based on respiratory action of a breathing cycle of the person. As one possibility, when the body cavity is the pleural cavity, pressure between the body cavity and the one or more one-way valves swings from positive to negative during the breathing cycle. Based on these fluctuations in pressure between the body cavity and the one or more one-way valves, the one or more one-way valves will close during inspiration (when pressure is negative) and open during expiration (when pressure is positive). As such, in an example, the valve assembly can provide a pump action with energy provided by the respiratory action of the person draining fluid from the body cavity. Given this opening and closing due to respiratory action, the valve assembly can act as a pump to move fluid from the body cavity, through the tube, through the one or more one-way valves, and out the outlet.

In at least some implementations, the one or more one-way valves may each be configured to have a low "cracking pressure," such that the one-way valve is configured to transition from a closed state to an open state with relatively small differential pressures across the one-way valve. For instance, the cracking pressure of each one-way valve can range anywhere from about 25 $cmH_2O$ or less to about 5 $cmH_2O$ or less, and as specific examples, the cracking pressure of a given one-way valve could be less than about 25 $cmH_2O$, less than about 15 $cmH_2O$, less than about 10 $cmH_2O$, or less than about 5 $cmH_2O$. Further, in at least some implementations, the one or more one-way valves may also each be configured to have a low "resealing pressure," such that the one-way valve is configured to transition from an open state to a closed state with small differential pressures across the one-way valve. For instance, the resealing pressure of each one-way valve can range anywhere from about 15 $cmH_2O$ or less to about 2 $cmH_2O$ or less, and as specific examples, the cracking pressure of a given one-way valve could be less than about 15 $cmH_2O$, less than about 10 $cmH_2O$, less than about 5 $cmH_2O$, or less than about 2 $cmH_2O$.

Further yet, the cracking pressure and/or the resealing pressure for each of the one or more one-way valves may be selected based on any of various factors, an example of which may be the type of cavity from which the fluid-management system is intended to drain fluid, among other examples.

In operation, prior to draining the body cavity using the disclosed fluid-management system, a person may first select an external reservoir in which to drain the fluid from the body, such as a sink, a commode, and/or a container provided by the person, among other possibilities. Next, to initiate the draining process, the person may switch the adjustable outlet lock of the valve assembly to an unlocked position. When the adjustable outlet lock is in the unlocked position, fluid may begin moving through the fluid-management system due to the pressure of the body cavity and/or the pumping action provided by the valve assembly. This will move fluid from the cavity, through the tube extending from the cavity to the inlet of the system, through the one or more one-way valves of the system, and then out of the outlet of the system and into the external reservoir. After the draining process has begun, the person may drain the fluid from the cavity until the cavity is empty and/or a desired amount of fluid has been drained from the cavity. Finally, after draining is complete, the person may decontaminate the outlet and/or adjustable lock of the valve assembly and switch the adjustable lock into the locked position. Alternatively, the adjustable lock could be a locking cap that can be attached to the catheter assembly to seal the valve assembly and prevent fluid flow or removed to allow fluid flow. At the conclusion the cap can be decontaminated and reattached or a new cap can be attached.

The disclosed fluid-management system may also be designed such that, when a sufficient amount of fluid has moved through the fluid-management system, a siphon effect can be utilized to help to more quickly drain the fluid from the cavity. For instance, the disclosed fluid-management system may be designed such that the pressure of the body cavity and/or pumping action provided by the valve assembly may allow a column of fluid to form within the tube that in turn leads to a siphon effect. The height of this column of fluid can be increased by the patient sitting up or standing or by lowering the distal end of the tube. In other words, the disclosed fluid-management system may be designed such that, once the tube is primed by the valve assembly, fluid from the cavity can be siphoned out.

As mentioned above, in some implementations, the one or more one-way valves of the valve assembly may take the form of a single one-way valve, whereas in other implementations, the one or more one-way valves of the valve assembly may take the form of two one-way valves arranged in series. As also mentioned above, in either of these arrangements, the one or more one-way valves are each configured to open and close based on fluctuations in pressure between a cavity of a person's body and the one-way valve, or fluctuations in pressure between a cavity of a person's body and the first one-way valve and fluctuations in pressure between the first one-way valve and the second one-way valve. Furthermore, in implementations where the one or more one-way valves of the valve assembly take the form of two one-way valves arranged in series, the two one-way valves may allow for additional capabilities and/or benefits relative to a valve assembly having a single one-way valve, including but not limited to improving the flow of fluid movement in the fluid-management system (e.g., when used together with a pumping chamber) and/or providing an additional barrier to retrograde flow, among other possibilities.

For instance, in at least some implementations, the two one-way valves of the valve assembly may be arranged in series within a pumping chamber, where a first one-way valve may be positioned on a first side of the pumping chamber proximate to the inlet of the valve assembly and a second one-way valve may be positioned on a second side of the pumping chamber proximate to the outlet of the valve assembly. Such a pumping chamber may be formed from a resiliently flexible material that may be compressed and decompressed to provide a pumping action to prime the fluid-management system and get fluid moving through the fluid-management system. In this respect, cyclical compression and decompression of the resiliently flexible material may draw fluid (e.g., liquid and/or air) from the inlet, through the first one-way valve into an interior space of the pumping chamber, through the second one-way valve, and out the outlet of the valve assembly. Such a two-valve configuration may thus allow a person to prime the fluid-management system, which may help to speed up the draining process by getting fluid to move more quickly through the fluid-management system. Such a two-valve configuration may also allow for the generation of supraphysiologic positive and/or negative pressures, which may also be of benefit to clear debris from within the tubing, from within the one-way valves, and/or from within other regions of the valve assembly.

The fluid-management system (and method of operation) disclosed herein may provide various benefits over existing fluid-management systems that allow a person to selectively control when to drain excess fluid from a body cavity to an external reservoir, such as a fluid-management system that is based on a dedicated pump-and-reservoir assembly.

For instance, the valve assembly of the disclosed fluid-management system is configured to leverage pressure gradients produced with respect to the body cavity and the valve system to drain fluid from the body cavity rather than relying on an active, vacuum-based pumping component (which involves larger, heavier, and more expensive components). Further, the valve assembly of the disclosed fluid-management system is not integrated into a dedicated pump-and-reservoir assembly and can be used to drain fluid from the body cavity into any available reservoir at any time. As a result, the disclosed fluid-management system is smaller, lighter, and more portable than existing fluid-management systems. The fluid-management system can thus remain with the person at all times (e.g., the external portion of the fluid-management system can be coiled and taped to a person's body or tucked into clothing when not in use) and does not require that the person have access to a dedicated pumping-and-reservoir assembly.

Further, given that the fluid-management system does not rely of an active, vacuum-based component and is not integrated into a dedicated pump-and-reservoir assembly, the disclosed fluid-management system is less costly (e.g., for persons using the assemblies and/or insurance companies for persons using the assemblies) than existing fluid-management systems.

Still further, by avoiding the need to attach a dedicated pump-and-reservoir assembly to the implanted tube and also detach the dedicated pump-and-reservoir assembly from the implanted tube each time a person drains the body cavity, the draining process using the disclosed fluid-management system is less cumbersome compared to draining processes using the existing fluid-management systems.

Yet still further, as noted above, the existing draining processes involve connecting components(s) of the dedicated pump-and-reservoir assembly to the attachment point of the implanted tube, which may be associated with a risk of contamination (e.g., if one or more of the components being attached is not sterile). By avoiding the need to attach a dedicated pump-and-reservoir assembly to the implanted tube and also detach the dedicated pump-and-reservoir assembly from the implanted tube each time a person drains the body cavity, the disclosed fluid-management system also reduces a risk of contamination compared to the existing fluid-management systems. And yet still further, as noted above, in existing fluid management systems, when the implanted tube is accessed, the systems do not actively prevent backflow during the draining process. The disclosed fluid-management system includes one or more one-way valves configured to prevent backflow in the fluid-management system both during the draining process as well as when the adjustable outlet lock is closed. Actively preventing backflow reduces a risk of contamination and/or infection compared to the existing fluid-management systems.

Accordingly, in one aspect, disclosed herein is a fluid-management system comprising a valve assembly and a tube for carrying fluid from a body cavity of a person to the valve assembly. The valve assembly is configured to be positioned external to the person's body and comprises (i) an inlet, (ii) an outlet, (iii) one or more one-way valves positioned between the inlet and outlet that are each configured to open and close based on fluctuations in pressure between the person's body cavity and the one-way valve, and (iv) an adjustable outlet lock configured to selectively prevent fluid movement through the outlet.

In another aspect, disclosed herein is a fluid-management system comprising a valve assembly and a tube for carrying fluid from a body cavity of a person to the valve assembly. The valve assembly is configured to be positioned external to the person's body and comprises (i) an inlet, (ii) an outlet, (iii) a plurality of one-way valves positioned between the inlet and outlet that are each configured to open and close based on fluctuations in pressure between the person's body cavity and the one-way valve, and (iv) an adjustable outlet lock configured to selectively prevent fluid movement through the outlet. In at least some implementations, the plurality of one-way valves may be arranged in series. Further, the tube is configured to extend from the inlet of the valve assembly to the person's body cavity.

In yet another aspect, disclosed herein is a method of operation of a fluid-management system comprising a valve assembly and a tube for carrying fluid from a body cavity of a person to the valve assembly. The valve assembly is positioned external to the person's body and comprises (i) an inlet, (ii) an outlet, (iii) one or more one-way valves positioned between the inlet and outlet that are each configured to open and close based on fluctuations in pressure between the person's body cavity and the one-way valve, and (iv) an adjustable outlet lock configured to selectively prevent fluid movement through the outlet. The method includes while the adjustable outlet lock is in a locked position, the adjustable outlet lock preventing fluid movement through the outlet. The method further includes while the adjustable outlet lock is in an unlocked position, each of the one or more one-way valves opening and closing based on fluctuations in pressure between the person's body cavity and the one-way valve, so as to provide a pumping action to move fluid from the body cavity through the tube, into the inlet, and out of the outlet to an exterior reservoir. In at least some implementations, the fluctuations occur based on respiratory action of a breathing cycle of the person.

In still yet another aspect, disclosed herein is a method for fluid management that includes providing a fluid-management system comprising a valve assembly and a tube for carrying fluid from a body cavity of a person to the valve assembly, where the valve assembly is configured to be positioned external to the person's body and comprises (i) an inlet, (ii) an outlet, (iii) one or more one-way valves positioned between the inlet and outlet that are each configured to open and close based on fluctuations in pressure between a cavity of a person's body and the one-way valve, and (iv) an adjustable outlet lock configured to selectively prevent fluid movement through the outlet. The method further includes implanting a portion of the fluid-management system into the person's body, such that a proximal end of the tube is in fluid communication with the cavity and the valve assembly is positioned external to the person's body.

One of ordinary skill in the art will appreciate these as well as numerous other aspects in reading the following disclosure.

BRIEF DESCRIPTION OF THE DRAWINGS

FIGS. 8A-D illustrate an example adjustable outlet lock, according to an example of the present disclosure.

DETAILED DESCRIPTION

The following disclosure makes reference to the accompanying figures and several example embodiments. One of ordinary skill in the art should understand that such references are for the purpose of explanation only and are therefore not meant to be limiting. Part or all of the disclosed systems, devices, and methods may be rearranged, combined, added to, and/or removed in a variety of manners, each of which is contemplated herein.

As mentioned above, current fluid-management systems and methods that allow a person to selectively control when to drain excess fluid from a body cavity such that such that an external reservoir is not always attached to the implanted tube that is in fluid communication with the body cavity have numerous drawbacks. The fluid-management methods and systems in accordance with the present disclosure beneficially provide improved methods and systems for draining fluid from a body cavity to an external reservoir. In particular, the methods and systems in accordance with the present disclosure beneficially provide for avoiding a need to attach a dedicated pump-and-reservoir assembly that includes an active pumping component for pumping fluid out of the body cavity and a drainage reservoir for collecting the pumped fluid. Rather, in accordance with the present disclosure, the components to initiate draining safely and effectively are on the person at all times, such that the person can selectively drain the body cavity.

In one example, a fluid-management system for selectively draining fluid from a body cavity includes a valve assembly and a tube for carrying fluid from a body cavity of a person to the valve assembly. The valve assembly is configured to be positioned external to the person's body and comprises (i) an inlet, (ii) an outlet, (iii) one or more one-way valves positioned between the inlet and outlet that are each configured to open and close based on fluctuations in pressure between the person's body cavity and the one-way valve, and (iv) an adjustable outlet lock configured to selectively prevent fluid movement through the outlet. The fluid-management system may be used by a person to drain fluid into any appropriate external reservoir. Body fluid to be drained may comprise liquid, gas, or a combination of liquid and gas.

Figure 1B:
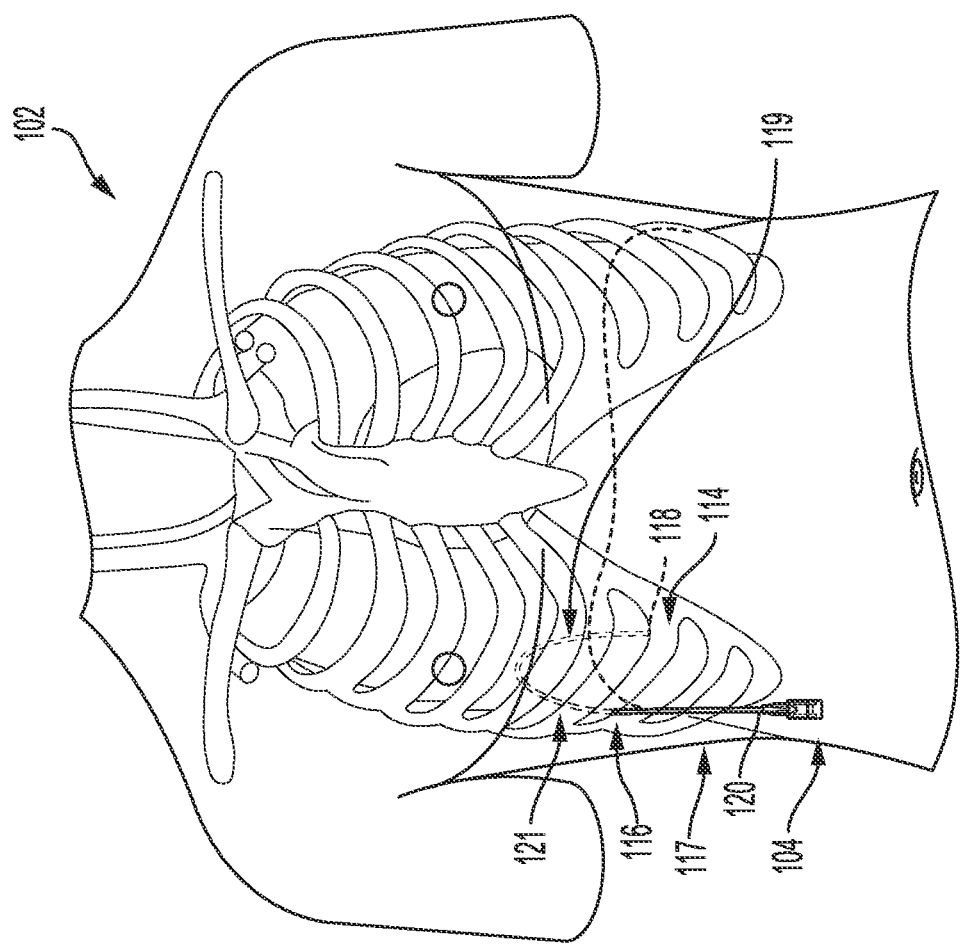
FIG. 1B illustrates the example fluid-management system of FIG. 1A implanted in a person.
Figure 1A:
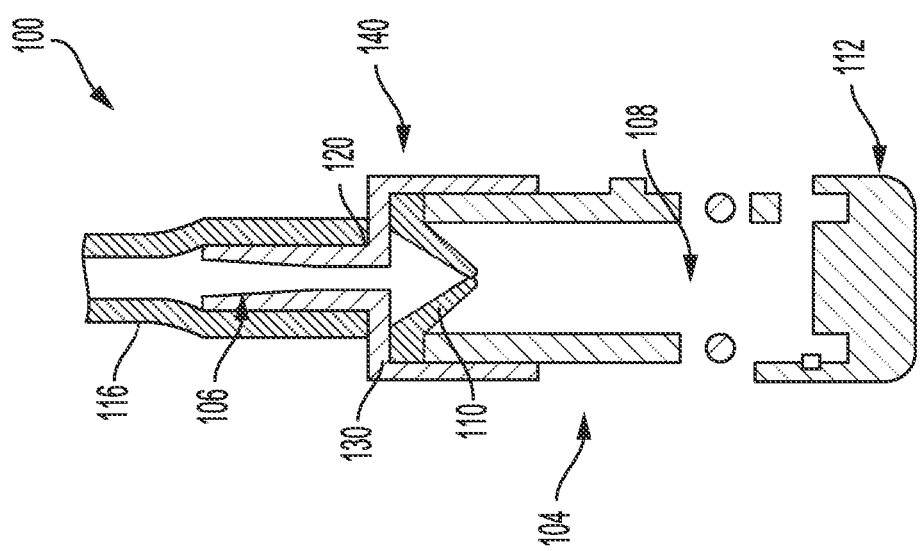
FIG. 1A illustrates an example fluid-management system, according to an example of the present disclosure.

Turning now to the figures, FIG. 1A depicts an example fluid-management system 100, and FIG. 1B depicts the fluid-management system 100 implanted in a person's body 102. Fluid-management system 100 includes a valve assembly 104 having an inlet 106, an outlet 108, a one-way valve 110, and an adjustable outlet lock 112. One-way valve 110 is positioned between inlet 106 and outlet 108 and is configured to open and close based on fluctuations in pressure between cavity 114 and one-way valve 110. Fluid-management system 100 also includes a fluid-management tube 116 for carrying fluid from cavity 114 to valve assembly 104. Tube 116 is configured to extend from inlet 106 to cavity 114 and allow movement of fluid from cavity 114 to inlet 106 of valve assembly 104. Tube 116 is implanted in person's body 102, such that a proximal end 118 of tube 116 is positioned within cavity 114 and a distal end 120 of tube 116 is positioned external to body 102. Further, valve assembly 104 is positioned external to the person's body 102. In particular, with reference to FIG. 1A, external portion 117 of fluid-management system 100 is positioned external to person's body 102. Further, in the example illustrated, the internal portion of fluid-management system 100 includes a first portion 119 of tube 116 positioned behind the ribs and within cavity 114, a second portion 121 of tube 116 positioned in front of the ribs within person's body 102. Other example arrangements of the inner and external portions of fluid-management system 100 are possible as well.

One-way valve 110 includes a one-way valve frame 130 enclosing and providing structure and support to one-way valve 110. Further, one-way valve frame 130 may also serve to connect to distal end 120 of tube 116. The size and shape of the one-way valve frame 130 can be designed to provide joining points or interconnectable joints to tube 116. In an example, valve assembly 104 is non-removably attached to tube 116. As used herein, the term "non-removably attached" means that a first component (e.g., the valve assembly) is intended not to be removed from a second component (e.g., the tube) during normal use and cannot be readily removed from the second component without the use of extraordinary force and/or tools.

Cavity 114 may be a cavity in person's body 102 that may build up fluid for which there is a desire or need to selectively drain out of the body. In the example of FIG. 1A, cavity 114 is a pleural cavity of person's body 102. However, other body cavities are possible, such as a peritoneal cavity, a cerebrospinal cavity, a pericardial cavity, a breast cavity, or a cavity of a cystic lesion, among other possibilities.

Adjustable outlet lock 112 is configured to selectively prevent fluid movement through outlet 108. In particular, adjustable outlet lock 112 is configured to move between a locked position in which adjustable outlet lock 112 seals outlet 108 and an unlocked position in which the adjustable outlet lock 112 allows fluid movement through outlet 108. Adjustable outlet lock 112 may be controlled by a person such that the person may keep adjustable outlet lock 112 in the locked position when not draining cavity 114. Further, the person may switch adjustable outlet lock 112 to the unlocked position when the person wishes to drain cavity 114.

In the example of FIG. 1A, adjustable outlet lock 112 is located at outlet 108 and is configured to cover outlet 108 when in the locked position. However, adjustable outlet lock 112 may be located in other positions, such as upstream of outlet 108. Further, in the example of FIG. 1A, adjustable outlet lock 112 takes the form of a cap and is locked by securely attaching the cap to outlet 108. In particular, the locked position of the cap corresponds to the cap being attached to outlet 108 (as seen in FIG. 1B), and the unlocked position corresponds to the cap being unattached from outlet 108 (as seen in FIG. 1A). Other adjustable outlet locks are possible, some examples of which are described in greater detail below.

As mentioned above, one-way valve 110 is configured to open and close based on fluctuations in pressure between cavity 114 of person's body 112 and one-way valve 110. By opening and closing based on fluctuations in pressure between cavity 114 and one-way valve 110, one-way valve 110 is able to allow fluid movement out of outlet 108 and also prevent retrograde flow (also referred to herein as "backflow") in fluid-management system 100 (e.g., flow of liquid and/or air back into tube 116). In practice, retrograde flow may result in aspiration of air back into cavity 114 (e.g., a pleural cavity) or flow of liquid back into the cavity 114, and such retrograde flow could cause various issues such as infection and/or collapse of the lung. Therefore, preventing backflow may help to avoid such issues that may be associated with flow of liquid and/or air back into tube 116. Further, in some examples, opening and closing of one-way valve 110 may also provide a pumping action that helps move fluid from cavity 114 and through tube 116 and valve assembly 104.

Figure 2A:
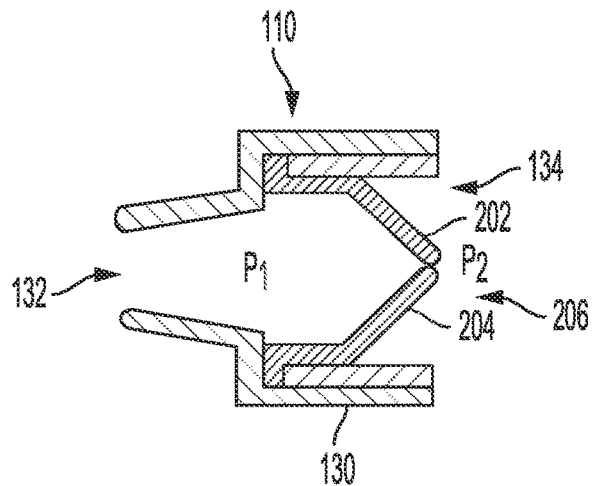
FIG. 2A illustrates a cross-sectional schematic view of a one-way valve in a closed state.
Figure 2B:
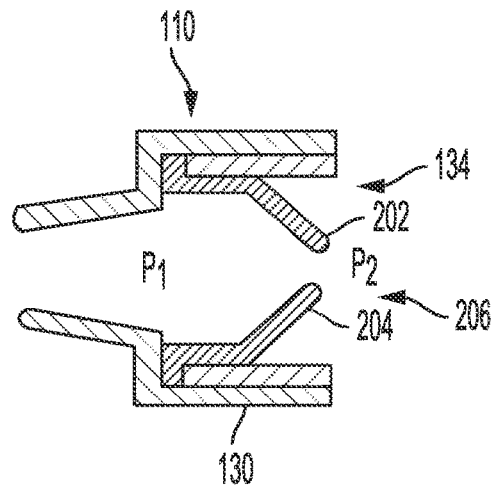
FIG. 2B illustrates a cross-sectional schematic view of a one-way valve in an open state.

Opening and closing of one-way valve 110 is generally described with respect to FIGS. 2a-b. FIG. 2a shows one-way valve 110 in a closed state, whereas FIG. 2b shows one-way valve 110 in an open state. When one-way valve 110 is in a closed position as shown in FIG. 2a, the pressure differential across valve 110 is such that $P_1 \leq P_2+P_C$, where $P_1$ is the pressure on a first side 132 of one-way valve 110, $P_2$ is the pressure on a second side 134 of one-way valve 110, and $P_C$ is the cracking pressure of one-way valve 110. Similarly, when one-way valve 110 is in an open position as shown in FIG. 2b, the pressure differential across valve 110 is such that $P_1 > P_2+P_C$, where $P_1$ is the pressure on first side 132 of one-way valve 110, $P_2$ is the pressure on second side 134 of one-way valve 110, and $P_C$ is the cracking pressure of one-way valve 110. In this instance, with $P_1 > P_2+P_C$, fluid would flow from first side 132 through one-way valve 110 to second side 134.

In an example, one-way valve 110 may be configured to have a low cracking pressure, such that the one-way valve is configured to transition from a closed state to an open state with relatively small differential pressures across the one-way valve. For instance, the cracking pressure of one-way valve 110 can range anywhere from about 25 cmH$_2$O or less to about 5 cmH$_2$O or less, and as specific examples, the cracking pressure of a given one-way valve could be less than about 25 cmH$_2$O, less than about 15 cmH$_2$O, less than about 10 cmH$_2$O, or less than about 5 cmH$_2$O. Further, in an example, one-way valve 110 may be configured to have a low resealing pressure, such that the one-way valve is configured to transition from an open state to a closed state with small differential pressures across the one-way valve. For instance, the resealing pressure of one-way valve 110 can range anywhere from about 15 cmH$_2$O or less to about 2 cmH$_2$O or less, and as specific examples, the cracking pressure of a given one-way valve could be less than about 15 cmH$_2$O, less than about 10 cmH$_2$O, less than about 5 cmH$_2$O, or less than about 2 cmH$_2$O.

Further yet, the cracking pressure and/or the resealing pressure for one-way valve 110 may be selected based on any of various factors, an example of which may be the type of cavity from which the fluid-management system is intended to drain fluid, among other examples. For instance, as one possibility, in situations where pressures vary from low positive to low negative (e.g., pleural cavity), the cracking pressure and/or the resealing pressure may be kept lower than in situations in which pressures tend to remain positive (e.g., peritoneal cavity). As another possibility, in situations where pressures in a cavity tend to remain positive but it is desired to not let fluid volume drop to zero, the valve cracking pressure may be selected at a level configured to keep fluid in the cavity. For example, for the cerebospinal cavity, the cerebospinal cavity tends to remain positive pressure but it is desirable to not let cerebrospinal fluid (CSF) drop to zero. Thus, for the cerebospinal cavity, the valve cracking pressure may be set to a desirable level that will keep the fluid pressure in that space from dropping below the desired cracking pressure and would keep CSF in the cerebospinal cavity.

In an example, one-way valve 110 may include a plurality of lips that define a slit that can move from a closed position to an open position. For instance, with reference to FIGS. 2A-B, one-way valve 110 may include first lip 202 and second lip 204 that define slit 206. The lips 202 and 204 may be configured such that, when the lips are in the closed position, the surface area of interaction between the lips is relatively small. For instance, in an example, the surface area of interaction is below 60 mm$^2$ and preferably in a range 0.6 mm$^2$ to 6 mm$^2$. A surface area in this range may help ensure that the one-way valve works well both when wet and dry. As the surface area of interaction of valve lips becomes large (e.g., larger than 60 mm$^2$), significant cohesive and adhesive forces may develop between the liquid and the two surfaces when the lips are wetted, thereby making it more difficult for the valve to open. This force required to separate the two surfaces of the valve lips is given by the relationship, $$F = \frac{2 \cdot T \cdot A}{h},$$

where F=the force required to separate the lips, T is the surface tension of the wetting liquid (T=70 for water at 37° C.), A is the area of the interface between the lips and h is the thickness of the liquid layer between the lips.

In the example of FIGS. 2A-2B, one-way valve 110 is formed as a duckbill valve. However, other types and/or shapes of valves are possible as well, including, for instance, a flapper valve and a cross-slit valve, among other possibilities.

Further, in an example, one-way valve 110 is configured such that, when in the open state, the opening is larger than the lumen of tube 116. Such a configuration may help to ensure that any debris that can get into the tube can clear through the valve. In some examples, the opening at proximal end 118 of tube 116 is smaller than the lumen of tube 116, the lumen of tube 116 is smaller than the opening of one-way valve 110 when it is in the open state, and the opening of one-way valve 110 when it is in the open state in turn is smaller than the lumen of outlet 108. Other examples are possible as well.

Figure 3:
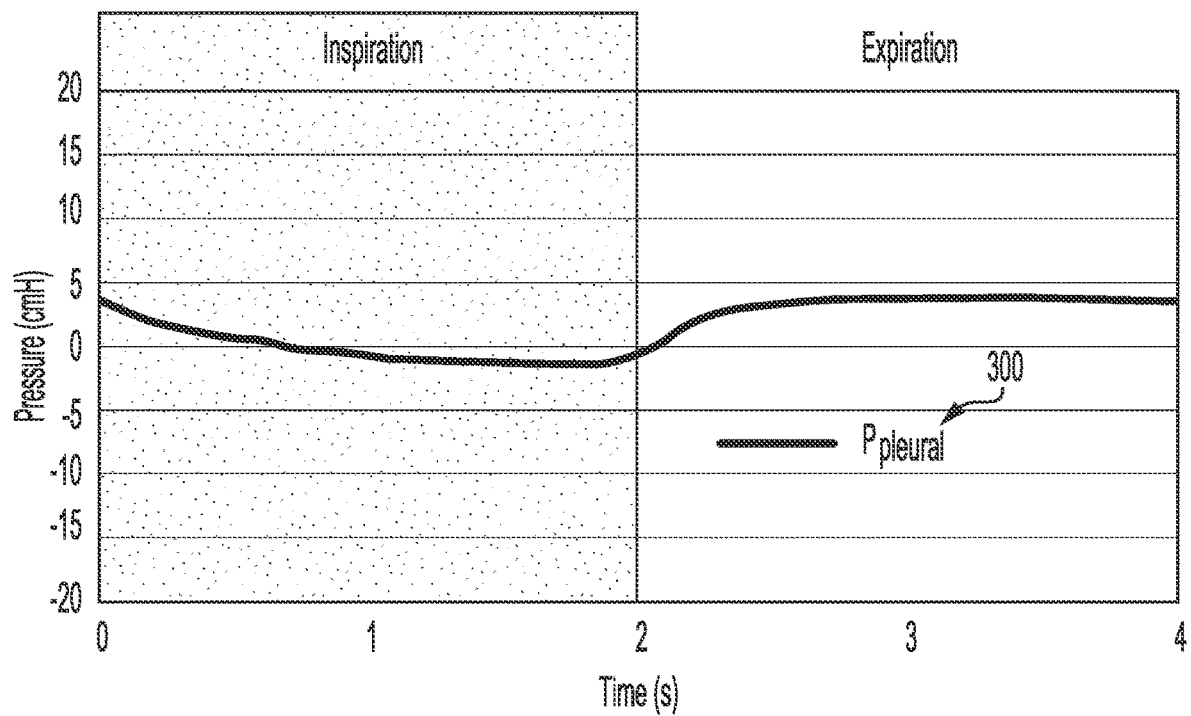
FIG. 3 shows representative pleural pressures as they change during inspiration and expiration.

In operation of fluid-management system 100, fluctuations in pressure between cavity 114 and one-way valve 110 may cause one-way valve 110 to open and close. In one example, the fluctuations in pressure between cavity 114 and one-way valve 110 occur based on respiratory action of a breathing cycle of the person. For instance, when cavity 114 is the pleural cavity, pressure between cavity 114 and one-way valve 110 swings from positive to negative during the breathing cycle. FIG. 3 illustrates an example pressure fluctuation that may occur between cavity 114 and one-way valve 110 during a breathing cycle. Pressures in the pleural cavity are not static and typically vary during normal breathing. As seen in FIG. 3, pleural pressure ($P_{pleural}$) 300 relative to atmospheric pressure swings from slightly negative during inspiration to slightly positive during expiration. During inspiration, external intercostal muscles contract leading to elevation of the ribs and sternum, and the diaphragm contracts, flattening out and pressing down on the abdominal contents. This combined action leads to an expansion of the thoracic cavity with a decrease in the pleural pressure that expands the elastic lung. Expiration during normal breathing is largely a passive process relying on elastic recoil. During expiration, the external intercostal muscles and the diaphragm simply relax. With relaxation of the external intercostals, the elasticity of the inflated lungs causes them to recoil back to their original position. This action leads to a decrease in size of the thoracic cavity with an increase in the pleural pressure.

The fluctuations in pleural pressure can be accentuated in some situations, such as situations where a person is breathing deeply and/or coughing. Based on these fluctuations in pressure between cavity 114 and one-way valve 110, one-way valve 110 will close during inspiration (when pressure is negative) and one-way valve 110 will open during expiration (when pressure is positive). As such, the valve assembly 104 provides a pump action with energy provided by the respiratory action of the person draining fluid from cavity 114 such that one-way valve 110 can allow flow of fluid from cavity 114 to outside during expiration and prevent backflow during inspiration. In particular, given this opening and closing due to respiratory action, valve assembly 104 can act as a pump to move fluid from cavity 114, through tube 116, through one-way valve 110, and out outlet 108. Further, since the pleural cavity is transiently moving positive to negative in pressure, one-way valve 110 also prevents backflow as valve assembly 104 provides the pumping action. When a person breathes in, one-way valve 110 closes and thus acts as check valve to prevent fluid and/or air from entering tube 116. On the other hand, when a person breathes out, the pleural pressure increases and forces fluid to move forward.

An example draining process for draining body cavity 114 is described below. Prior to draining body cavity 114 using fluid-management system 100, a person may first select an external reservoir in which to drain the fluid from cavity 114. In general, the person may drain the fluid into any appropriate reservoir such as a sink, a commode, and/or a container provided by the person, among other possibilities. Further, prior to initiating drainage, the valve assembly area may be cleaned with soap and water and/or decontaminated with alcohol, betadine, or chlorhexidine, among other possibilities. Next, to initiate the draining process, the person may switch adjustable outlet lock 112 to the unlocked position. When adjustable outlet lock 112 is in the unlocked position, fluid may begin moving through fluid-management system 100. As described above, one-way valve 110 may open and close based on fluctuations in the pressure between cavity 114 and one-way valve 110. In practice, when adjustable outlet lock 112 is in the locked position, the one-way valve 110 is typically closed since typically $P_1 \leq P_2 + P_C$.

Upon initially unlocking the adjustable outlet lock 112, fluid may begin moving through fluid-management system 100 due to the pressure of body cavity 114 and/or the pumping action provided by the opening and closing of one-way valve 110. This will move fluid from cavity 114, through tube 116, through one-way valve 110, and then out of outlet 108 and into the external reservoir selected by the person. After the draining process has begun, the person may drain the fluid from cavity 114 until cavity 114 is empty and/or a desired amount of fluid has been drained from cavity 114. Finally, after draining is complete, the person may clean or decontaminate outlet 108 and/or adjustable outlet lock 112 and switch adjustable outlet lock 112 into the locked position.

Fluid-management system 100 may also be designed such that, when a sufficient amount of fluid has moved through fluid-management system 100, a siphon effect can be utilized to help to more quickly drain the fluid from cavity 114. For instance, fluid-management system 100 may be designed such that the pressure of cavity 114 and/or pumping action provided by valve assembly 104 may allow a column of fluid to form within the tube that in turn leads to a siphon effect. In other words, fluid-management system 100 may be designed such that, once tube 116 is primed by valve assembly 104 (e.g., based on the respiratory action), fluid from cavity 114 can be siphoned out.

Fluid-management system 100 may allow fluid from cavity 114 to be siphoned out when conditions suitable for siphoning occur. In general, siphoning may occur when (i) tube 116 has a sufficient column of fluid in tube 116 and (ii) the end of the column of fluid is lower than the fluid level in cavity 114, which provides a sufficient hydrostatic pressure gradient.

During draining, a person may control the level of outlet 108 in order to facilitate the end of the column of fluid being lower than the fluid level in cavity 114. Ensuring that the tube is held a sufficient amount below the fluid level may facilitate siphoning during the draining process.

The column of fluid needed to generate a siphon effect may vary. Within examples, a sufficient column of fluid may be a column of fluid having a length within the range of 10-100 centimeters (cm). Further, a longer tube may provide a longer column of fluid, which in turn may provide a stronger siphon effect and thus provide a quicker flow of fluid to more quickly drain fluid from cavity 114. In an example, after siphoning begins during a draining process, the person may continue draining fluid from cavity 114 until the cavity 114 is empty and/or a desired amount of fluid is removed from cavity 114. When siphoning is taking place, one-way valve 110 remains open. Finally, after draining is complete, the person may clean and/or decontaminate outlet 108 and/or adjustable outlet lock 112 of valve assembly 104 and move adjustable outlet lock 112 into the locked position. In some examples, the one-way valves, tubing diameter, and/or tubing length can be selected so as to ensure a desired minimum flow rate, such as 25 milliliters per minute (ml/min), 50 ml/min, 75 ml/min, 100 ml/min, 150 ml/min or greater, among other possibilities. Additionally or alternatively, the one-way valves (and associated cracking pressures), tubing length, and/or tubing diameter can be selected to prevent the pressure in the fluid cavity dropping below a desired level, such as −10 cmH$_2$O, −20 cmH$_2$O, −30 cmH$_2$O, or −40 cmH$_2$O or more negative, among other possibilities. In an example, for the pleural space, persons can have pain when the pressure is too low, have coughing fits, and there are reports of "reexpansion pulmonary edema" occurring when large volumes are drained and/or the pressure is too low. Preventing the pressure in the fluid cavity from dropping below a desired level may help to avoid or reduce such issues.

In some examples, the cavity pressure of the cavity being drained may tend to remain positive rather than fluctuate from positive to negative based on respiratory action of a person's breathing cycle. For instance, peritoneal cavity pressure relative to atmospheric pressure tends to remain positive throughout the breathing cycle. As such, in an example where the body cavity being drained is the peritoneal cavity, the pressure between cavity 114 and one-way valve 110 may tend to remain positive. In such a case, one-way valve 110 may not routinely open and close to provide a pump action to move fluid through the tube 116. Rather, in such a case, when adjustable outlet lock 112 is switched to the unlocked position, the positive peritoneal-cavity pressure may tend to cause fluid to move forward throughout the tube and to keep one-way valve 110 open. However, in situations where the cavity pressure may tend to remain positive, fluctuations in pressure may still occur for various reasons that may cause one-way valve 110 to close. For instance, the cavity pressure may, for one reason or another, fluctuate to negative. As one possibility, if the body position and/or tip of tube 116 were positioned to be such that the abdomen was lower than the tube outlet, the pressure could drop to negative. As another possibility, if the space (e.g., peritoneal space) was diseased such that the bowel/abdominal wall could not expand/shift as fluid is drained, a negative pressure could generate. As yet another possibility, a large release of gas (volume shift) from the abdomen could transiently transition pressure to negative. Other examples are possible as well. In such a case where the cavity pressure may tend to remain positive but fluctuations in pressure may still occur for various reasons that may cause one-way valve 110 to close, rather than providing a pumping action during the draining process, one-way valve 110 may instead serve primarily as a backstop to ensure that, if pressure fluctuates during the draining process to a negative pressure for some reason, one-way valve 110 closes to prevent backflow.

In the examples discussed above, the valve assembly 104 includes a single one-way valve. In other examples, the valve assembly 104 includes two one-way valves arranged in series, and the two one-way valves may allow for additional capabilities and/or benefits relative to a valve assembly having a single one-way valve. An example fluid-management system including a valve assembly having two one-way valves is described further with reference to FIGS. 4A-B.

Figure 4B:
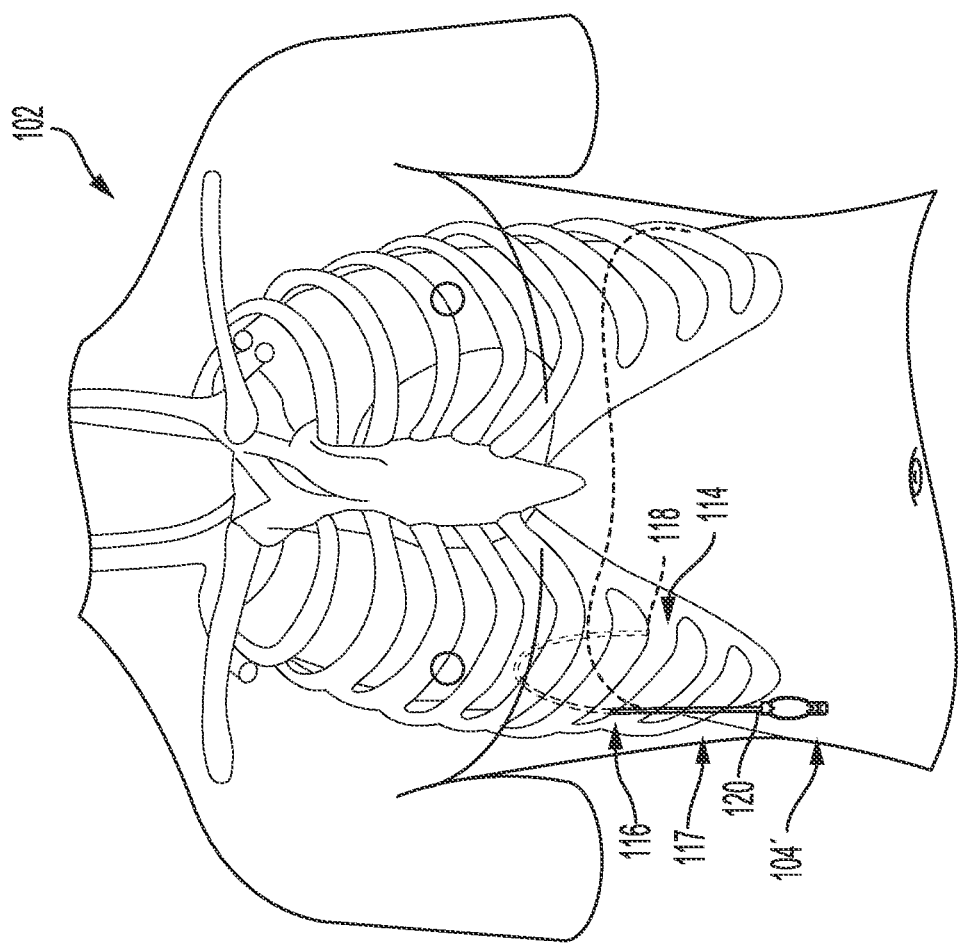
FIG. 4B illustrates the example fluid-management system of FIG. 4A implanted in a person.
Figure 4A:
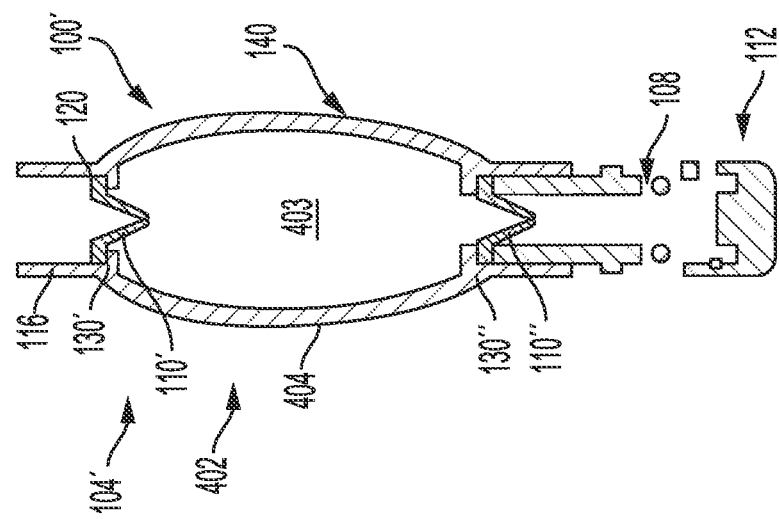
FIG. 4A illustrates an example fluid-management system, according to an example embodiment.

FIG. 4A depicts an example fluid-management system 100' and FIG. 4B depicts the fluid-management system 100' implanted in a person's body 102. Fluid-management system 100' includes a valve assembly 104' having an inlet 106, and outlet 108, one-way valves 110' and 110", and an adjustable outlet lock 112. One-way valves 110' and 110" are arranged in series and are housed in a pumping chamber 402 or on the proximal and distal ends of pumping chamber 402. One-way valves 110' and 110" are positioned between inlet 106 and outlet 108 and are each configured to open and close based on fluctuations in pressure between cavity 114 and the one-way valve. Further, one-way valve 110' is configured to open and close based on changes in cavity 114 pressure and pressure on an inside 403 of chamber 402, and one-way valve 110" is configured to open and close based on changes in pressure on inside 403 of chamber 402 (which may change based on cavity pressure and opening of one-way valve 110') and atmospheric pressure. Fluid-management system 100' also includes a fluid-management tube 116 for carrying fluid from cavity 114 to valve assembly 104'. Tube 116 is configured to extend from inlet 106 to cavity 114 and allow movement of fluid from cavity 114 to inlet 106 of valve assembly 104'. Tube 116 is implanted in person's body 102, such that a proximal end 118 of tube 116 is positioned within cavity 114 and a distal end 120 is positioned external to body 102. Further, valve assembly 104' is positioned external to the person's body 102.

As mentioned above, the one-way valves 110' and 110" are arranged in series and are housed in pumping chamber 402 or on the proximal and distal ends of pumping chamber 402. In an example, the main body 404 of pumping chamber may form and/or house one-way valve frames 130' and 130", which enclose and provide structure and support to one-way valves 110' and 110", respectively. In the example of FIG. 4A, the one-way valve frame 130' is integral with tube 116. In other examples, one-way valve frame 130' may serve to connect to distal end 120 of tube 116 (e.g., in a similar fashion as illustrated in FIG. 1A). The size and shape of the one-way valve frame 130' can be designed to provide joining points or interconnectable joints to tube 116. In an example, valve assembly 104' is non-removably attached to tube 116.

The valve assembly 104' may operate is a similar fashion as the valve assembly 104 described with respect to FIGS. 1-3. Furthermore, valve assembly 104' provides some additional capabilities for draining fluid from cavity 114. For instance, valve assembly 104' may provide additional capabilities and/or benefits relative to a valve assembly having a single one-way valve, including but not limited to improving the flow of fluid movement in the fluid-management system and/or providing an additional barrier to retrograde flow, among other possibilities.

Turning first to operating in a similar fashion as valve assembly 104, each of valves 110' and 110" may operate in the same fashion and have the same properties as one-way valve 110 of FIG. 1A. For instance, one-way valves 110' and 110" are each configured to open and close based on fluctuations in pressure between a cavity of a person's body and the one-way valve. As one example, fluctuations in pressure (e.g., fluctuations that occur based on respiratory action of a breathing cycle of the person) between cavity 114 and one-way valves 110' and 110" may cause one-way valves 110' and 110" to open and close, thereby providing a pumping action to move fluid. Given that one-way valves 110' and 110" are the same or similar in many respects to one-way-valve 110, one-way valves 110' and 110" thus are not described in as great of detail. It should be understood, however, that any of the possibilities and permutations described with respect to one-way valve 110 are also possible with respect to one-way valves 110' and 110".

Turning next to the additional capability of creating fluid movement in the fluid-management system 100', the pumping chamber 402 of valve assembly 104' can be used to prime the system and get fluid moving through fluid-management system 100'. Such a two-valve configuration may allow a person to prime the fluid-management system, which may help to speed up the draining process by getting fluid to move more quickly through the fluid-management system, which in turn may get the siphon effect to occur more quickly.

Such priming of fluid-management system 100' may be useful in various situations. For example, such priming of the system may be useful if the pumping action provided by the respiratory action is not sufficient to get fluid moving and/or does not get fluid moving as quickly as a person desires. As another example, such priming of the system may be useful if there is low positive pressure between cavity 114 and one-way valves 110', 110" that is insufficient to get fluid moving and/or does not get fluid moving as quickly as a person desires. As yet another example, such priming of the system may be useful if for some reason air is in the tube. In tubes common in catheter applications, a small amount of air can generate enough surface tension to air lock the tube. Priming of fluid-management system 100' may help overcome such generated airlocks. As still yet another example, such priming of fluid-management system 100' may be useful if there is not a sufficient hydrostatic pressure gradient to provide for a siphon effect. Other examples are possible as well.

Such a two-valve configuration may also allow for the generation of supraphysiologic pressures (both positive by compressing and negative by design of the resilience of the pump chamber 402) that may also be of benefit to clear potential obstructions and/or debris from the fluid-management system 100' (e.g., within the tubing, from within the one-way valves, or from within other regions of the valve assembly 104').

Figure 5A:
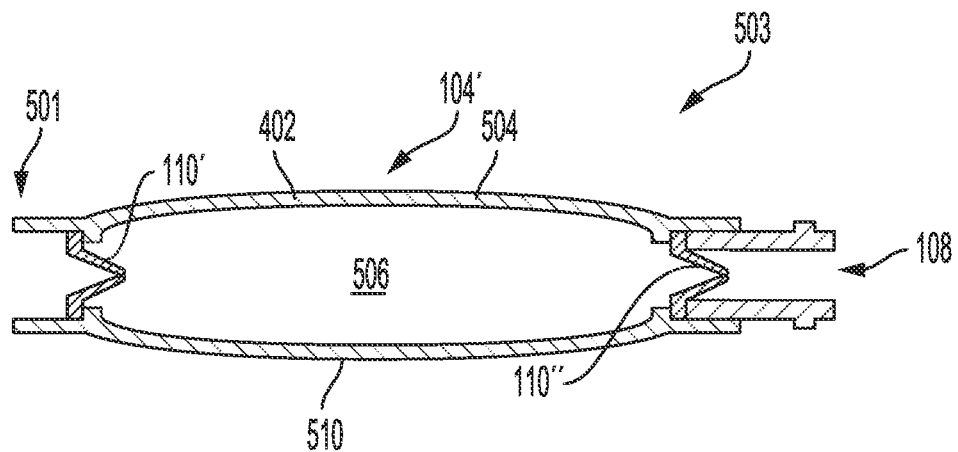
FIGS. 5A-D illustrates a pumping chamber of the fluid-management system of FIG. 4A at various stages of compression and decompression.

Priming of fluid-management system 100' using pumping chamber 402 is described further with respect to FIGS. 5A-D. FIG. 5A shows a cross-sectional schematic view of valve assembly 104' in a generally or substantially non-compressed state with both one-way valve 110' and one-way valve 110" closed. For clarity, one-way valve 110' is also referred to herein as an "inlet one-way valve," and one-way valve 110" is referred to as an "outlet one-way valve." Inlet one-way valve 110' is positioned on a first side 501 of pumping chamber 402 proximate to the inlet of valve assembly 104' and outlet one-way valve 110" is positioned on a second side 503 of pumping chamber 402 proximate to outlet 108 of valve assembly 104.

Figure 5B:
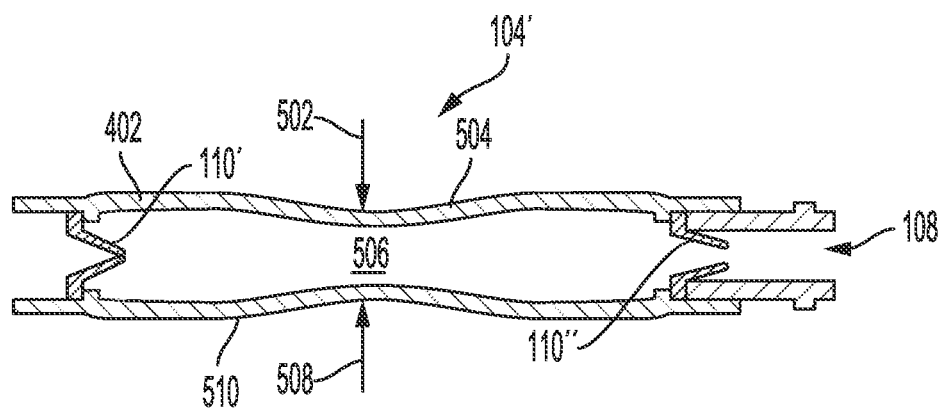

FIG. 5B shows a cross-sectional schematic view of valve assembly 104' in a generally or substantially compressed state. In an example, as shown, a first force 502 may act on a first wall 504 causing first wall 504 to collapse in towards interior space 506. Correspondingly, a second force 508 may additionally or alternatively act on a second wall 510 causing second wall 510 to collapse in towards interior space 506.

First force 502 and second force 508 may be applied to pumping chamber 402 in any suitable fashion. As one possibility, a person using fluid-management system 100' may supply the forces by manually compressing pumping chamber with their fingers. As another possibility, valve-system 104' may include an electromechanical actuator configured to apply forces 502 and 508. For instance, valve assembly 104' may include a piezoelectric diaphragm connected to the body of pumping chamber 402. The piezoelectric diaphragm may be activated and inactivated by a controller, and both the piezoelectric diaphragm 540 and the controller 530 may be powered, e.g., by a battery. As another example, valve assembly 104' may include a piston or cam configured to apply forces 502 and 508 to pumping chamber 402. Other example methods and systems for applying forces 502 and 508 are possible as well.

The collapse of the first wall 504 and/or second wall 510 serves to decrease the volume of interior space 506 and to increase the pressure in interior space 506. This increase in pressure causes inlet one-way valve 110' to remain closed and causes outlet one-way valve 110" to open, and fluid located in interior space 506 to flow from interior space 506 through outlet one-way valve 110" and out outlet 108. For incompressible fluids, the change of volume experienced by interior space 506 in response to the collapse of first wall 504 and/or second wall 510 will be approximately equal to the volume of fluid that moves from interior space 506 through outlet one-way valve 110". As the fluid moves from interior space 506 through outlet one-way valve 110", the pressure in interior space 506 will decrease. Once the interior pressure equals or substantially equals the pressure in outlet 108, flow will stop and outlet one-way valve 110" will close as shown in FIG. 5C.

Figure 5C:
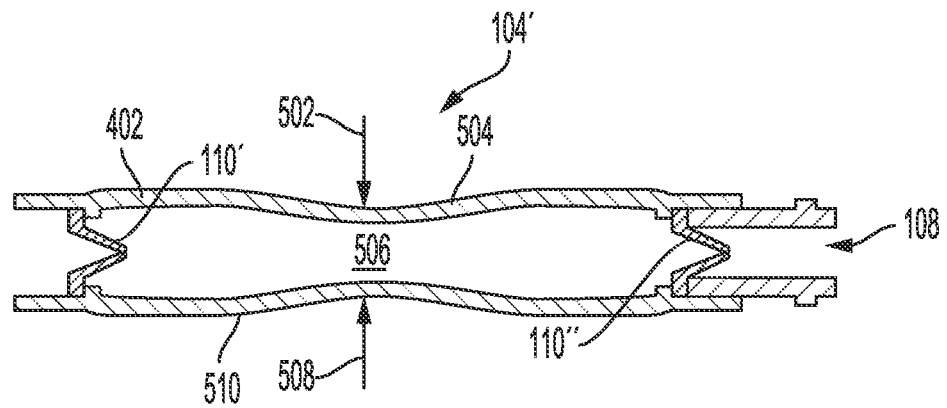
Figure 5D:
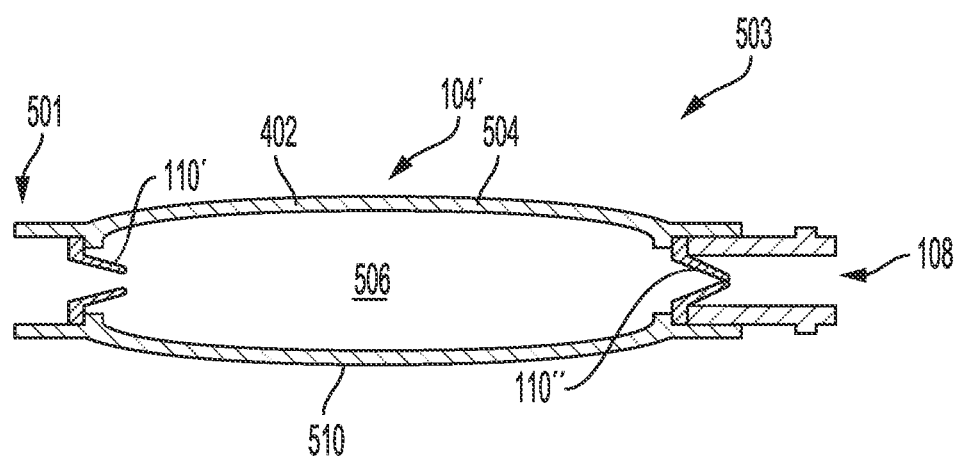

As described above, the body of pumping-chamber 402 may be substantially resiliently flexible and therefore, after being placed in a compressed state as shown in FIGS. 5B and 5C, valve assembly 104' will return to an uncompressed state as shown in FIG. 5D when at least one of the first force 502 and the second force 508 are removed. As the first wall 504 returns to its uncompressed state as the first force 502 is removed and/or the second wall 510 returns to its uncompressed state as the second force 508 is removed, the volume of the interior space 506 increases and the pressure in the interior space 506 decreases. The pressure inside the interior space 506 eventually drops below the pressure on the inlet 501 near inlet one-way valve 110' and causes inlet one-way valve 110' to open and fluid located in the inlet to flow into the interior space 506. In this way, valve assembly 104' operates as a pump that, generally, draws fluid from inlet 501 and passes it to outlet 108.

In some examples, pumping chamber 402 may be made of material that allows for pumping chamber 402 to be compressed and then freely returned to its original state. Pumping chamber 402 may be made of any suitable material. For example, pumping chamber 402 may be a resiliently flexible tube or cylinder made of polyurethane, silicone, polyvinyl chloride, or latex rubber. Alternatively, pumping chamber 402 may be made of a combination of two or more materials where at least one of the component materials provides resilience and at least one of the component materials provides fluid containment. For example, pumping chamber 402 may be composed of an elastic nitinol, steel, polyester, or other elastic component to provide for resiliency and a second fluid containment component such as polyurethane, silicone, polyvinyl chloride, latex rubber, polyethylene terephthalate, nylon, polytetrafluoroethylene, PEBAX, or the like to provide fluid containment within pumping chamber 402. In other examples, such as examples where valve assembly 104' includes an electromechanical actuator (e.g., a piezoelectric diaphragm, piston, or cam configured to apply forces 502 and 508 to pumping chamber 402), the material may be flexible but not resilient (or having limited resilience), as the an electromechanical actuator may provide both active compression and active rarefication.

Turning next to the additional barrier to retrograde flow, the addition of the second one-way valve provides another barrier to retrograde flow. In the example a FIG. 1A, one-way valve 110 provides a barrier to retrograde flow, whereas in the example of FIG. 4a, each of one-way valves 110' and 110" provide a barrier to retrograde flow. This additional barrier to retrograde flow may provide increased protection against retrograde flow.

In order to prevent blocking or clogging of the disclosed fluid-management system, one or more components of the fluid-management system may be coated in anticoagulation factors or fibrinolytic factors. For example, the components or surfaces of valve assemblies 104, 104' and/or implanted tube 116 may be coated at least in part with anticoagulation factors or fibrinolytic factors. For instance, with reference to FIG. 1A, internal portions of a body 140 of valve assembly 104, one-way valve 110, and/or internal portions of tube 116 may be coated in anticoagulation factors or fibrinolytic factors. Further, with reference to FIG. 4A, internal portions of pumping chamber 402, one-way valves 110' and 110", and/or internal portions of tube 116 may be coated in anticoagulation factors or fibrinolytic factors. Other components may be coated with anticoagulation factors or fibrinolytic factors as well.

The presence of the anticoagulation factors may reduce the amount of clotting that would otherwise occur if they were not present. Examples of anticoagulation factors include heparin, low molecular weight heparin, fondaparinux, idraparinux, idrabiotaparinux, diabigatran, rivaroxaban, apixan, betrixaban, edoxaban, darexaban, letaxaban, eribaxaban, hirudin, lepirudin, bivalirudin, argatroban, dabigatran, ximelagatran, hementin, vitamin E, coumarin, warfarin, acenocoumarol, phenprocoumon, atromentin, phenindione, brodifacoum, and difenacoum. Examples of fibrinolytic factors include plasmin, tissue plasminogen activator, urokinase, streptokinase, plasminogen activator inhibitor-1 inhibitor, and plasminogen activator inhibitor-2 inhibitor. Other examples of anticoagulation factors or fibrinolytics may be used.

In at least some implementations of the valve assembly 104' with pumping chamber 402, one-way valves 110' and 110" may each be configured to have a low "cracking pressure," such that the one-way valve is configured to transition from a closed state to an open state with relatively small differential pressures across the one-way valve. For instance, the cracking pressure of each one-way valve can range anywhere from about 25 cmH$_2$O or less to about 5 cmH$_2$O or less, and as specific examples, the cracking pressure of a given one-way valve could be less than about 25 cmH$_2$O, less than about 15 cmH$_2$O, less than about 10 cmH$_2$O, or less than about 5 cmH$_2$O. Further, in at least some implementations, the one-way valves 110' and 110" may also each be configured to have a low "resealing pressure," such that the one-way valve is configured to transition from an open state to a closed state with small differential pressures across the one-way valve. For instance, the resealing pressure of each one-way valve can range anywhere from about 15 cmH$_2$O or less to about 2 cmH$_2$O or less, and as specific examples, the cracking pressure of a given one-way valve could be less than about 15 cmH$_2$O, less than about 10 cmH$_2$O, less than about 5 cmH$_2$O, or less than about 2 cmH$_2$O. In other implementations of valve assembly 104' with pumping chamber 402, the cracking and/or resealing pressures of one-way valves 110' and 110" may be higher.

Pumping chamber 402 is described with reference to examples where the one or more one-way valves take the form of two one-way valves arranged in series. In some examples where valve assembly 104 includes a single one-way valve, the valve assembly 104 may further include a compressible chamber positioned on the inlet or outlet side of the single one-way valve, such as positioned between the single one-way valve and a small narrowing in the lumen of the flow pathway which may provide hydrostatic resistance. Such a compressible chamber can be used to help initiate fluid flow and/or to enhance or allow a pumping action.

Figure 6A:
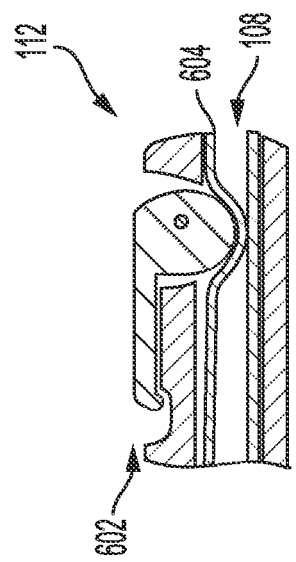
FIGS. 6A-B illustrate an example adjustable outlet lock, according to an example of the present disclosure.
Figure 6B:
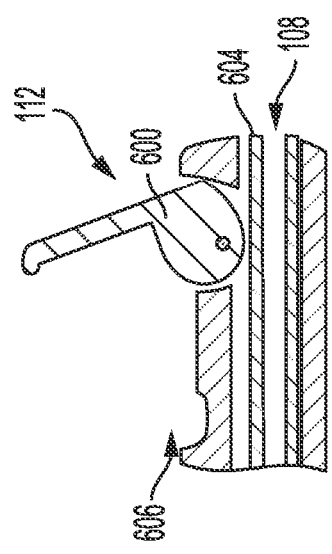

As mentioned above, in the example of FIG. 1A, adjustable outlet lock 112 takes the form of a cap, but various adjustable outlet locks 112 are possible. As one possibility, adjustable outlet lock 112 may take the form of a pinch lever. For instance, with reference to FIGS. 6A-B, adjustable outlet lock 112 may include a lever 600 positioned at outlet 108 that may be adjusted to move the lever 600 between (i) a locked position 602 (see FIG. 6A) in which lever 600 pinches a tube 604 of outlet 108 in order to seal outlet 108 and (ii) an unlocked position 606 (see FIG. 6B) in which lever 600 no longer pinches tube 604, thus allowing tube 604 to open and thereby allowing fluid movement through outlet 108.

Figure 7A:
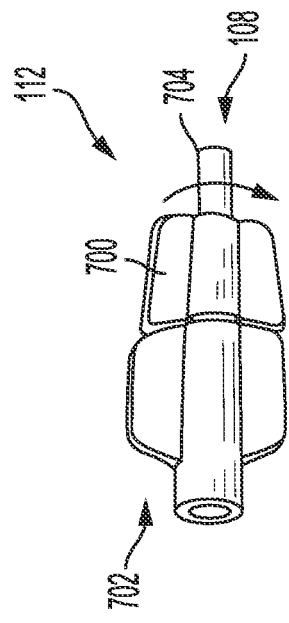
FIGS. 7A-B illustrate an example adjustable outlet lock, according to an example of the present disclosure.
Figure 7B:
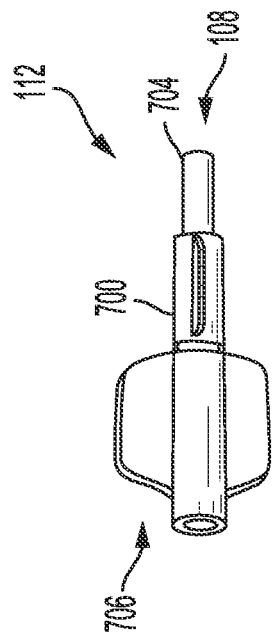

As another possibility, adjustable outlet lock 112 may take the form of a twist pinch. For instance, with reference to FIGS. 7A-B, adjustable outlet lock 112 may include a twist pinch 700 positioned at outlet 108 that may be adjusted to move twist pinch 700 between (i) a locked position 702 (see FIG. 7A) in which twist pinch 700 pinches a tube 704 of outlet 108 in order to seal outlet 108 and (ii) an unlocked position 706 in which twist pinch 700 no longer pinches tube 704, thus allowing tube 704 to open and thereby allowing fluid movement through outlet 108.

Figure 9A:
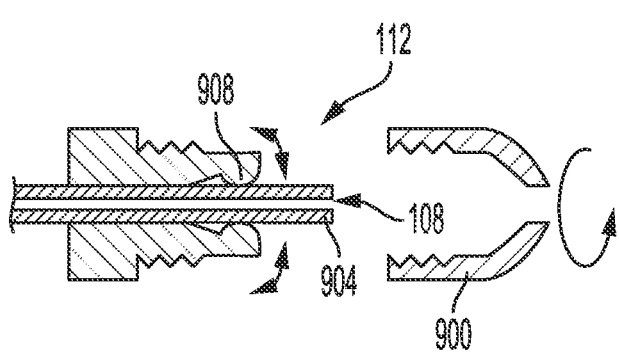
FIGS. 9A-C illustrate an example adjustable outlet lock, according to an example of the present disclosure.
Figure 9B:
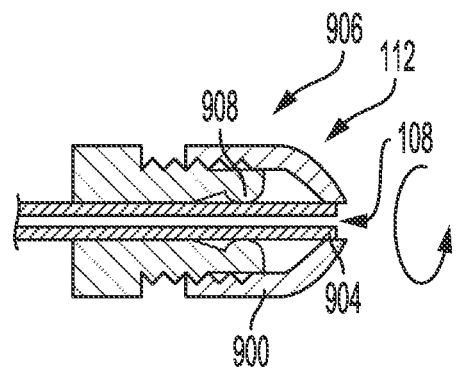
Figure 9C:
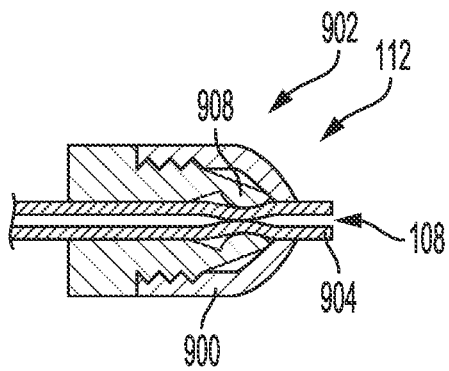

As yet another possibility, adjustable outlet lock 112 may take the form of a twist cap that activates pinch arms. For instance, with reference to FIGS. 8A-D, adjustable outlet lock 112 may include a twist cap 800 positioned at outlet 108 that may be adjusted to move twist cap 800 between (i) a locked position 802 (see FIG. 8C and FIG. 8D, which is a cross-sectional view of adjustable outlet lock 112 taken along line 8D-8D in FIG. 8C) in which twist cap 800 forces pinch arms 808 to pinch a tube 804 of outlet 108 in order to seal outlet 108 and (ii) an unlocked position 806 (see FIG. 8A and FIG. 8B, which is a cross-sectional view of adjustable outlet lock 112 taken along line 8B-8B in FIG. 8A) in which twist cap 800 allows pinch arms 808 to flex outward, thus allowing tube 804 to open and thereby allowing fluid movement through outlet 108. Another example twist cap that activates pinch arms is illustrated in FIGS. 9A-C. As shown, adjustable outlet lock 112 may include a threaded twist cap 900 positioned at outlet 108 that may be adjusted to move threaded twist cap 900 between (i) a locked position 902 (see FIG. 9C) in which threaded twist cap 900 forces pinch arms 908 to pinch a tube 904 of outlet 108 in order to seal outlet 108 and (ii) an unlocked position 906 (see FIG. 9B) in which threaded twist cap 900 allows pinch arms 908 to flex outward, thus allowing tube 904 to open and thereby allowing fluid movement through outlet 108. As shown in FIG. 9C, there is a partial conical taper on the inside of twist cap 900 that engages the pinch arms 908 when twist cap 900 is screwed all the way on that closes the pinch arms 908. Further, when twist cap is partially unscrewed (see FIG. 9B), the partial conical taper on the inside of twist cap 900 disengages and releases the pinch arms 108. Additionally, as indicated in FIGS. 9A-B, tube 904 may be opened when the inside of twist cap 900 disengages and releases the pinch arms 108 (see FIG. 9B), and, with continued unscrewing, twist cap 900 can be completely disengaged from pinch arms 908 (see FIG. 9A).

Figure 10A:
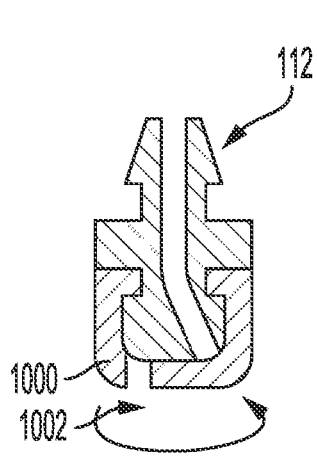
FIGS. 10A-B illustrate an example adjustable outlet lock, according to an example of the present disclosure.
Figure 10B:
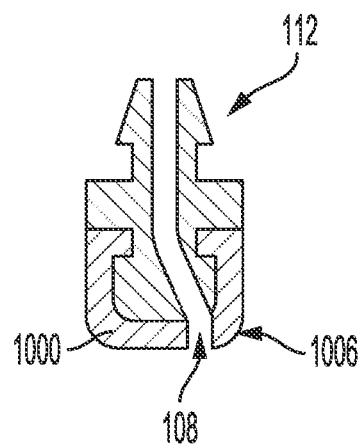

As yet another possibility, adjustable outlet lock 112 may take the form of an offset device. For instance, with reference to FIGS. 10A-B, adjustable outlet lock 112 may include an offset device 1000 positioned at outlet 108 that may be adjusted to move offset device 1000 between (i) a locked position 1002 (see FIG. 10A) in which offset device 1000 blocks outlet 108 in order to seal outlet 108 and (ii) an unlocked position 1006 (see FIG. 10B) in which offset device 1000 no longer blocks outlet 108 thereby allowing fluid movement through outlet 108.

Figures 11A, 11B:
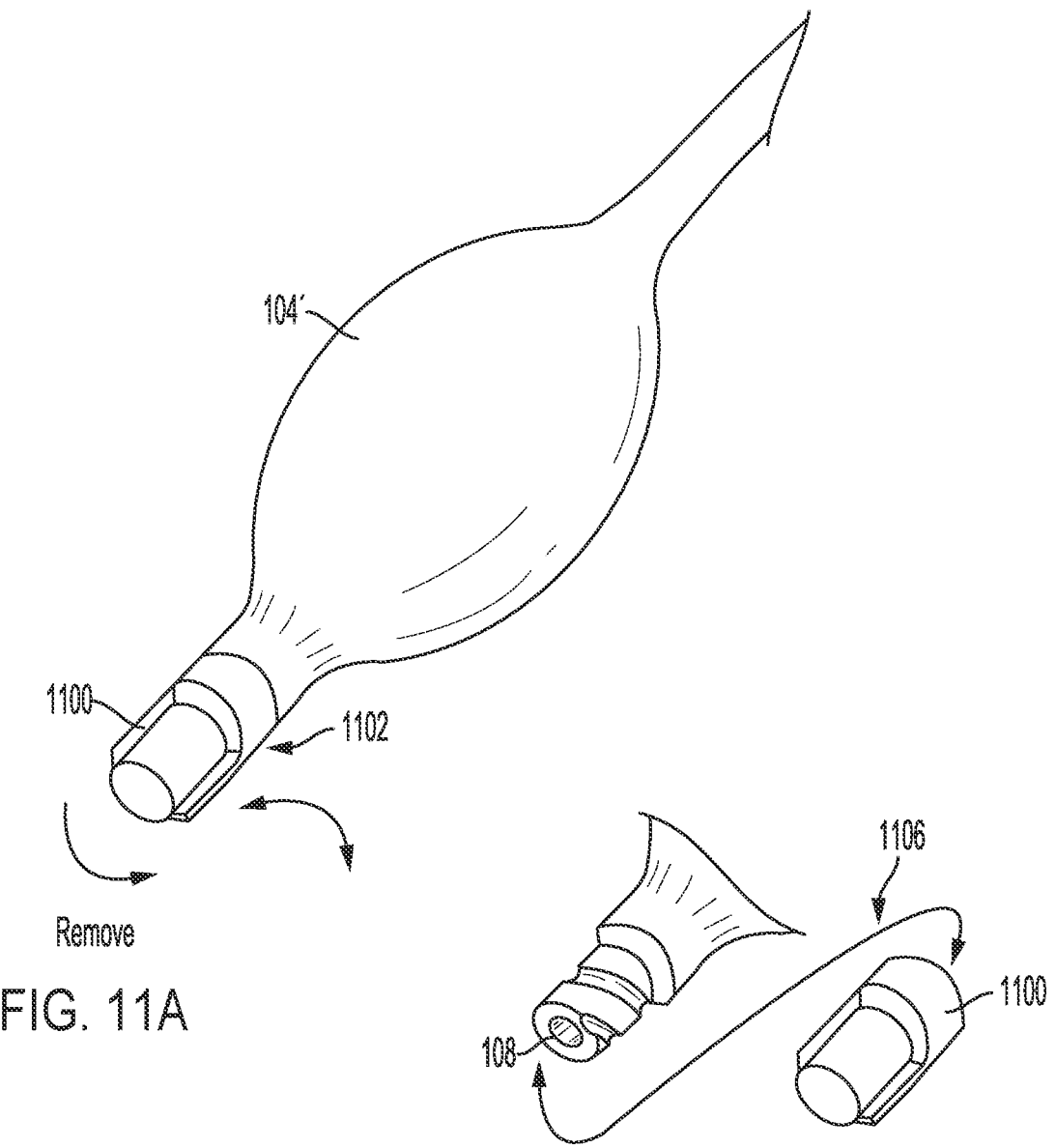
FIGS. 11A-B illustrate an example adjustable outlet lock, according to an example of the present disclosure.

FIGS. 11A-B illustrate yet another example adjustable outlet lock, which in this example is disposed on valve assembly 104'. In this example, adjustable outlet lock 112 takes the form of a removable locking cap 1100 positioned at outlet 108 that may be adjusted to move locking cap 1100 between (i) a locked position 1102 (see FIG. 11A) in which removable locking cap 1100 blocks outlet 108 in order to seal outlet 108 and (ii) an unlocked position 1106 in which removable locking cap 1100 no longer blocks outlet 108 thereby allowing fluid movement through outlet 108.

Figure 12A:
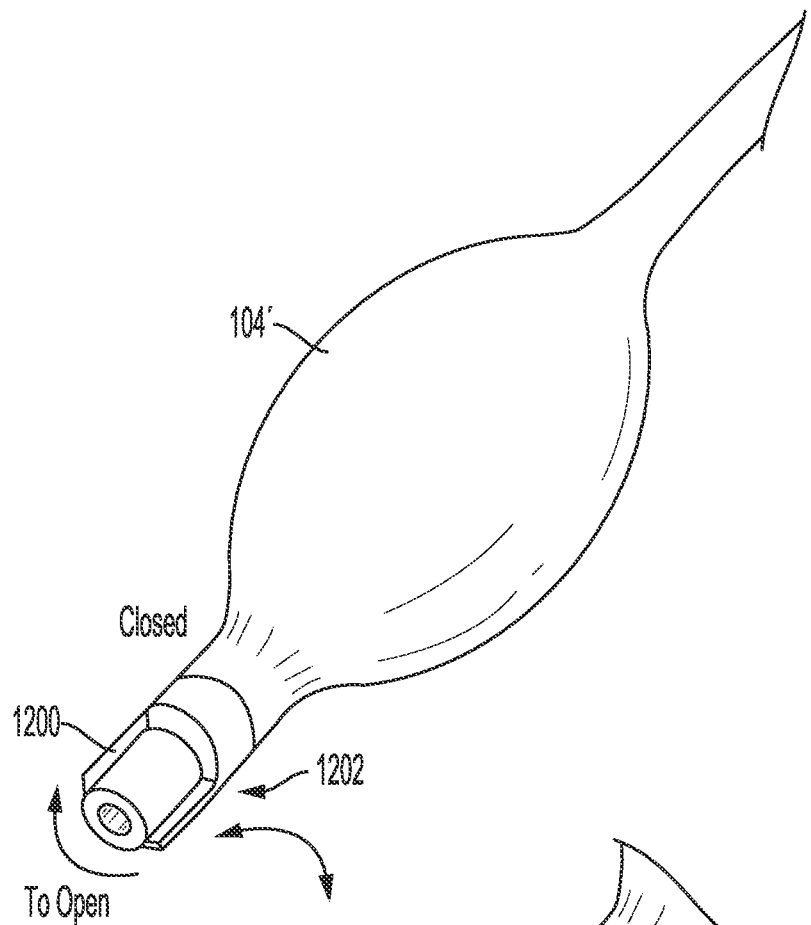
FIGS. 12A-B illustrate an example adjustable outlet lock, according to an example of the present disclosure.
Figure 12B:
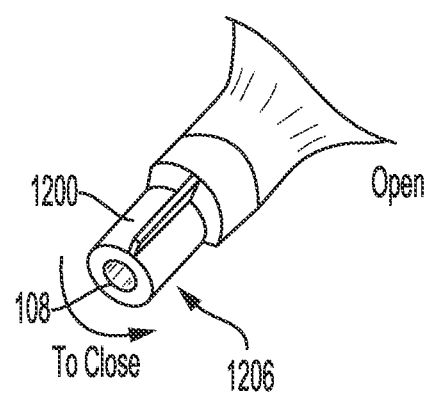

FIGS. 12A-B illustrate yet another example adjustable outlet lock, which in this example is disposed on valve assembly 104'. In this example, adjustable outlet lock 112 takes the form of a rotatable locking valve 1200 positioned at outlet 108 that may be adjusted to move rotatable locking valve 1200 between (i) a locked position 1202 (see FIG. 12A) in which rotatable locking valve 1200 blocks outlet 108 in order to seal outlet 108 and (ii) an unlocked position 1206 in which rotatable locking valve 1200 no longer blocks outlet 108 thereby allowing fluid movement through outlet 108.

Other example adjustable outlet locks are possible as well, including, for instance, ball-valves, and stop-cocks, and external clamps, among other possibilities. Further, in examples where the adjustable outlet lock comprises a removable cap, valve assembly 104 may also include a tether for the removable cap, so the removable cap remains attached to valve assembly 104 when a person is draining fluid from cavity 114 and the removable cap is in the unlocked position.

As mentioned above, a person may drain the fluid from cavity 114 until cavity 114 is empty and/or a desired amount of fluid has been drained from the cavity. The amount of fluid drained using fluid-management system 100 may depend on various factors, such as the cavity being drained, the amount of fluid in the cavity being drained, an amount of time available for draining, a recommend amount of fluid to drain, among other possibilities. In an example, when draining a pleural cavity, a person may drain approximately 100 to 200 milliliters per day. In another example, when drain a peritoneal cavity, a person may drain approximately 0.75 to 1.25 liters a day. Other examples are possible as well.

Figure 14:
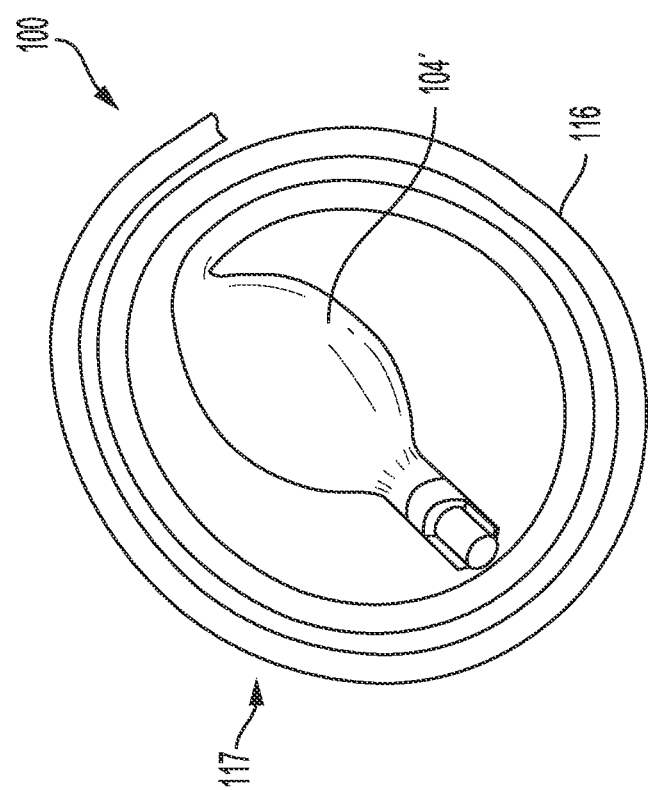
FIG. 14 illustrates an example arrangement of an external portion of a fluid-management system, according to an example of the present disclosure.
Figure 13:
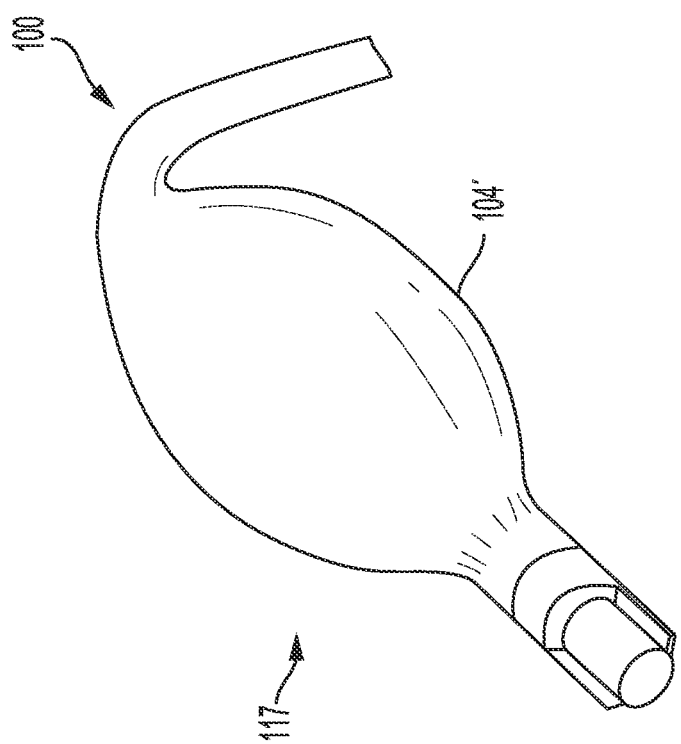
FIG. 13 illustrates an example arrangement of an external portion of a fluid-management system, according to an example of the present disclosure.

As mentioned above, the disclosed fluid-management system 100 can remain with the person at all times. When a person is not draining the body cavity, the person may secure the external portions of the fluid-management system to the person's body. For example, the external portion of the fluid-management system may be secured to the person (e.g., via an appropriate securing mechanism such as a gauze pad and/or medical tape, among other possibilities), such as external portion 117 of fluid-management system 100 shown in FIG. 13. In some examples, the person may coil the external portion of the implanted tube, so that the external portion of the fluid-management system may be secured to the person (e.g., via an appropriate securing mechanism such as a gauze pad and/or medical tape, among other possibilities). For instance, FIG. 14 depicts an example of such coiling. In particular, when a person is not draining the body cavity, the person may coil the external portion of implanted tube 116, so that the external portion 117 of fluid-management system 100 may be secured to the person. In cases where the external portion of the implanted tube may be coiled, the geometry of valve assembly 104 and/or pumping chamber 402 can be sized and shaped to facilitate positioning within the coiled implanted tube 116 and/or to minimize the profile of the secured fluid-management system.

Figure 15B:
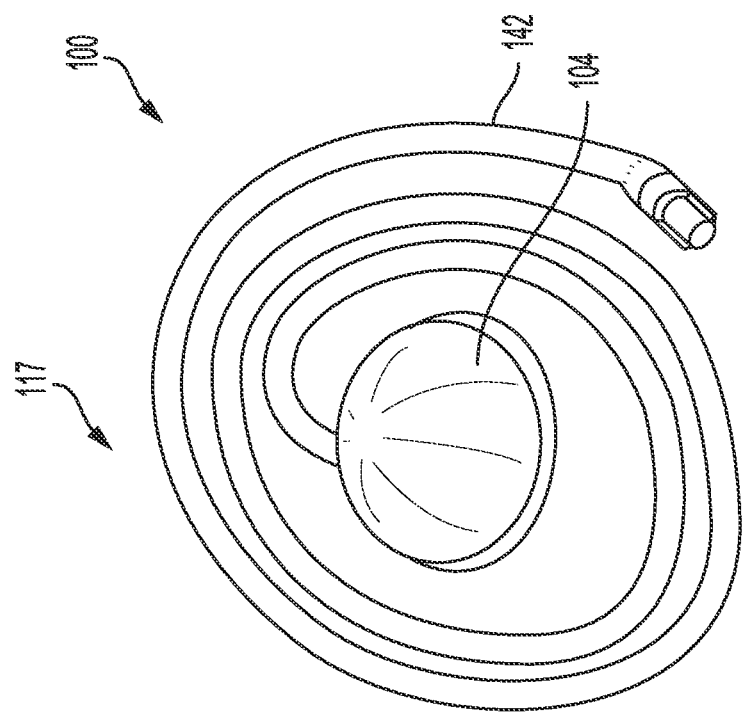
FIG. 15B illustrates an example arrangement of an external portion of the fluid-management system of FIG. 15A, according to an example of the present disclosure.
Figure 15A:
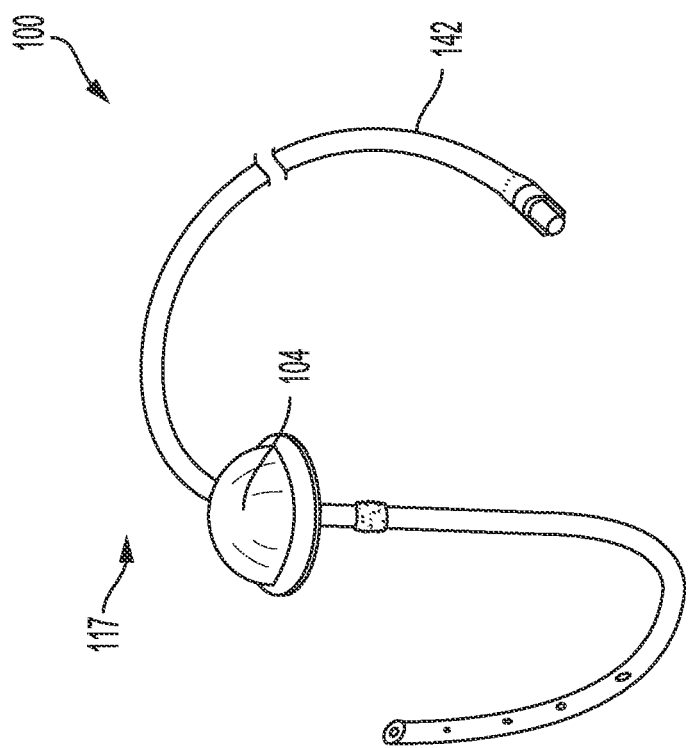
FIG. 15A illustrates an example fluid-management system, according to an example of the present disclosure.

Further, FIGS. 15A-B depict another example of coiling. In particular, FIG. 15A illustrates an example fluid-management system 100, and FIG. 15B illustrates an example arrangement of an external portion 117 of the fluid-management system. With reference to FIG. 15A, fluid management system 100 includes tube 116 for carrying fluid from a body cavity of a person to valve assembly 104 and external tube 142. In this example, tube 116 may be within or substantially within the person's body, while valve assembly 104 (including external tube 142) may be external to the person's body. In this situation, when a person is not draining the body cavity, the person may coil external tube 142, so that the external portion 117 of fluid-management system 100 may be secured to the person. In cases where the external tube may be coiled, the geometry of valve assembly 104 and/or pumping chamber 402 can be sized and shaped to facilitate positioning within coiled external tube 142 and/or to minimize the profile of the secured fluid-management system.

Figure 16:
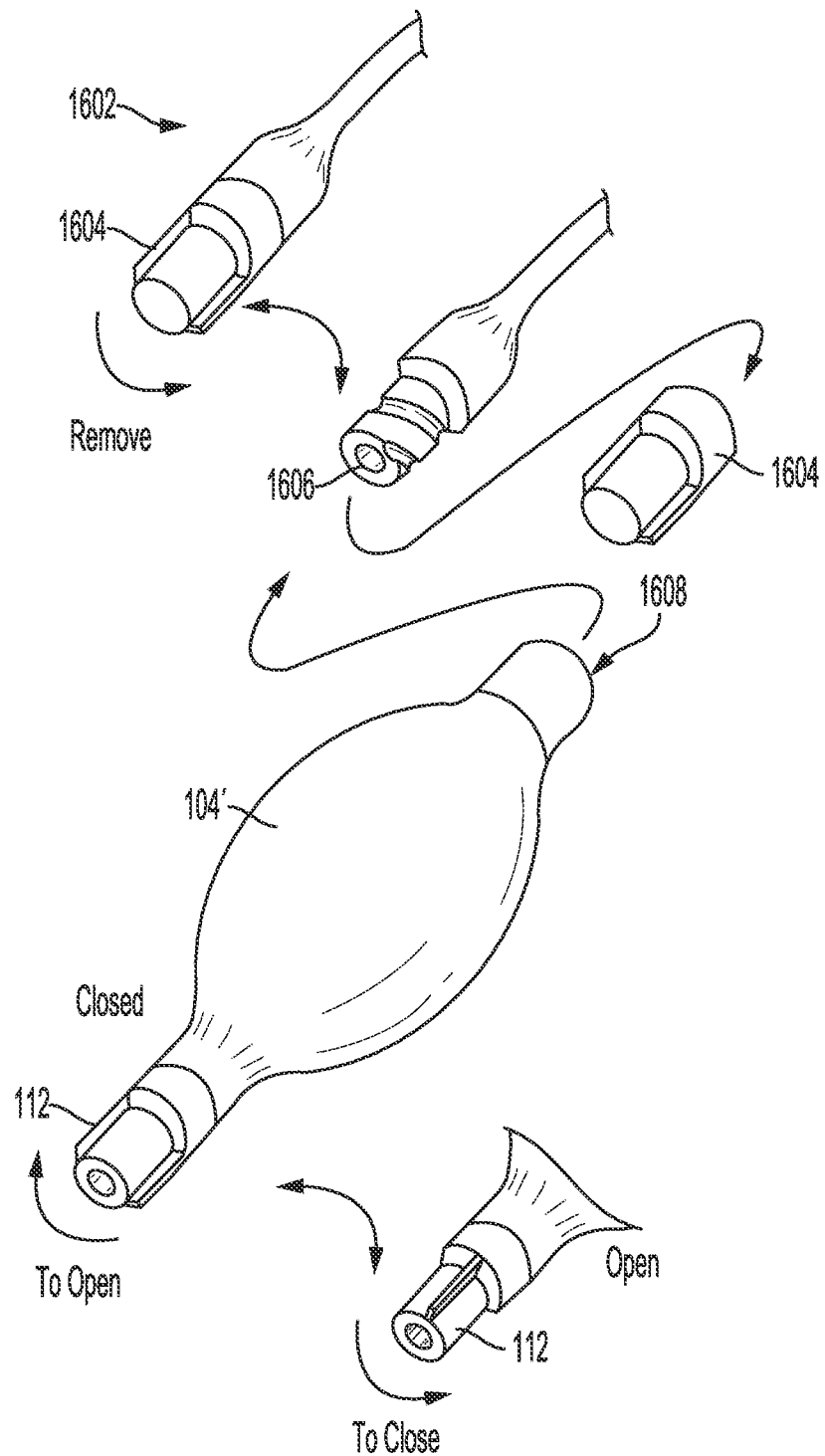
FIG. 16 illustrates an example process for connecting an example fluid-management system to an implanted tube, according to an example of the present disclosure.
Figure 17:
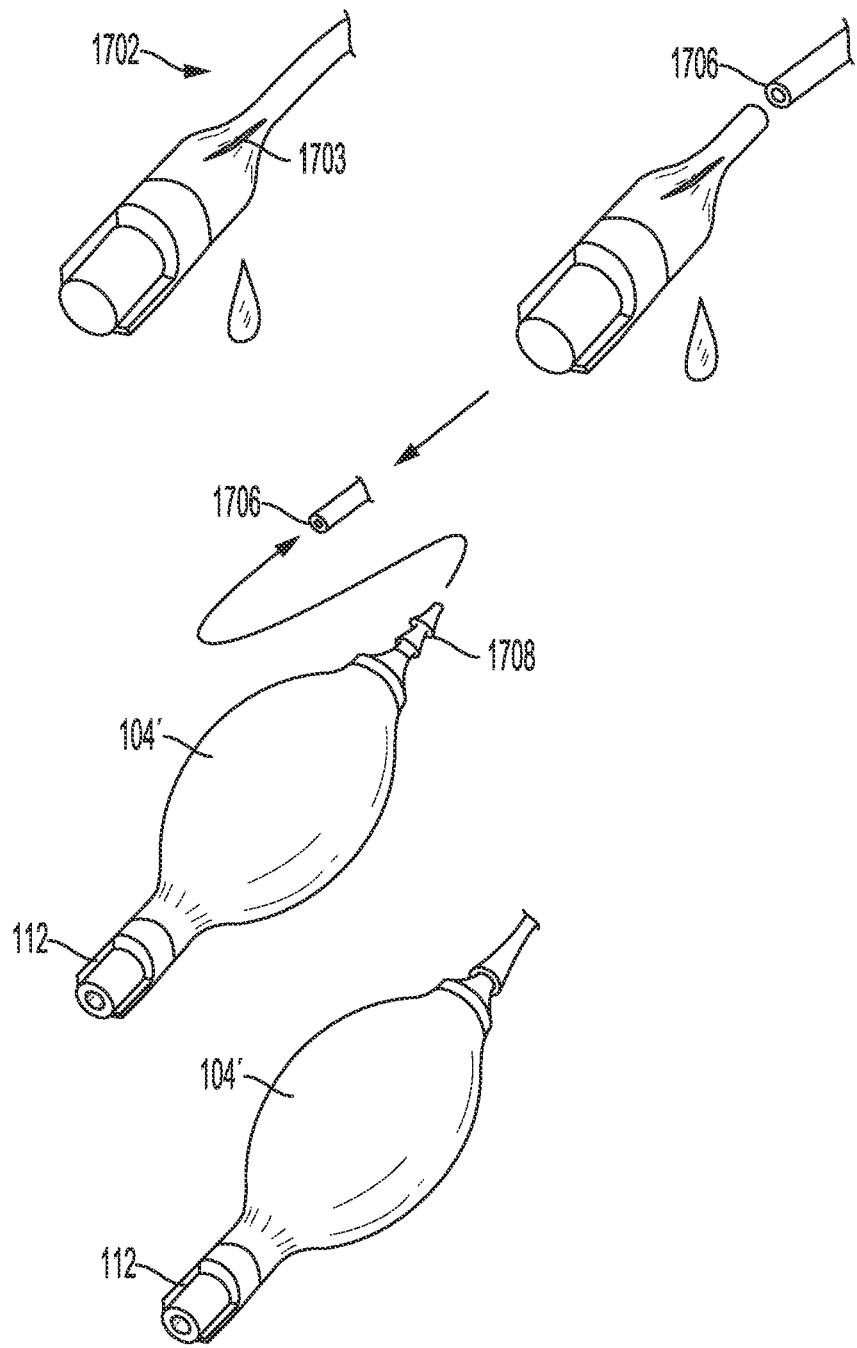
FIG. 17 illustrates an example process for connecting an example fluid-management system to an implanted tube, according to an example of the present disclosure.

In some examples, valve assembly 104 or valve assembly 104' may be connected to an indwelling catheter, such as an indwelling pleural catheter. In order to facilitate attachment to an indwelling catheter, valve assembly 104 or valve assembly 104' may include an attachment mechanism for attachment to the indwelling catheter. FIGS. 16 and 17 illustrate two examples of connecting an example fluid-management system including valve assembly 104' to an indwelling catheter.

Turning first to FIG. 16, FIG. 16 illustrates an example process for connecting valve assembly 104' to an indwelling catheter 1602. Indwelling catheter 1602 includes a locking cap 1604. Locking cap 1604 may be removed, thereby revealing distal end 1606 of indwelling catheter 1602. Valve assembly 104' may include (i) adjustable outlet lock 112 on a distal end of the valve assembly 104' and (ii) an attachment system 1608 on a proximal end of the valve assembly 104'. The attachment system 1608 is configured to attach to distal end 1606 of indwelling catheter. Any suitable attachment system for connecting to distal end 1606 is possible. In an example, a person may engage attachment system 1608 with distal end 1606 and twist the valve assembly 104' and/or attachment system 1608 so that attachment system 1608 connects to distal end 1606. After connecting valve assembly 104' to indwelling catheter 1602, a user may control adjustable outlet lock 112 (e.g., open and close adjustable outlet lock 112 as shown in FIG. 16) to drain fluid from the body cavity as desired.

Turning next to FIG. 17, FIG. 17 illustrates an example process for connecting valve assembly 104' to an indwelling catheter 1702. In this example, indwelling catheter 1702 may be damaged and leaking (e.g., through slit 1703 in indwelling catheter 1702). Indwelling catheter 1702 may be clamped of proximate to the person in which indwelling catheter 1702 is implanted, and indwelling catheter 1702 may then be cut cleanly, thereby removing the damaged section with slit 1703. Valve assembly 104' may include (i) adjustable outlet lock 112 on a distal end of the valve assembly 104' and (ii) an attachment system 1708 on a proximal end of the valve assembly 104'. The attachment system 1708 is configured to attach to distal end 1706 of the tubing of indwelling catheter 1702. Any suitable attachment system for connecting to distal end 1706 of the tubing is possible. In an example, attachment system 1708 may be configured to provide an interference fit with distal end 1706 of the tubing of indwelling catheter 1702. However, other attachment systems are possible as well. After connecting valve assembly 104' to indwelling catheter 1702, a user may control adjustable outlet lock 112 (e.g., open and close adjustable outlet lock 112) to drain fluid from the body cavity as desired.

Example methods for facilitating draining of fluid from a body cavity and for draining fluid from a body cavity are also provided. Such methods could, for example, be carried out by fluid-management systems 100 or 100' as described with reference to FIGS. 1-17 and/or utilizing fluid-management systems 100 or 100'.

Figure 18:
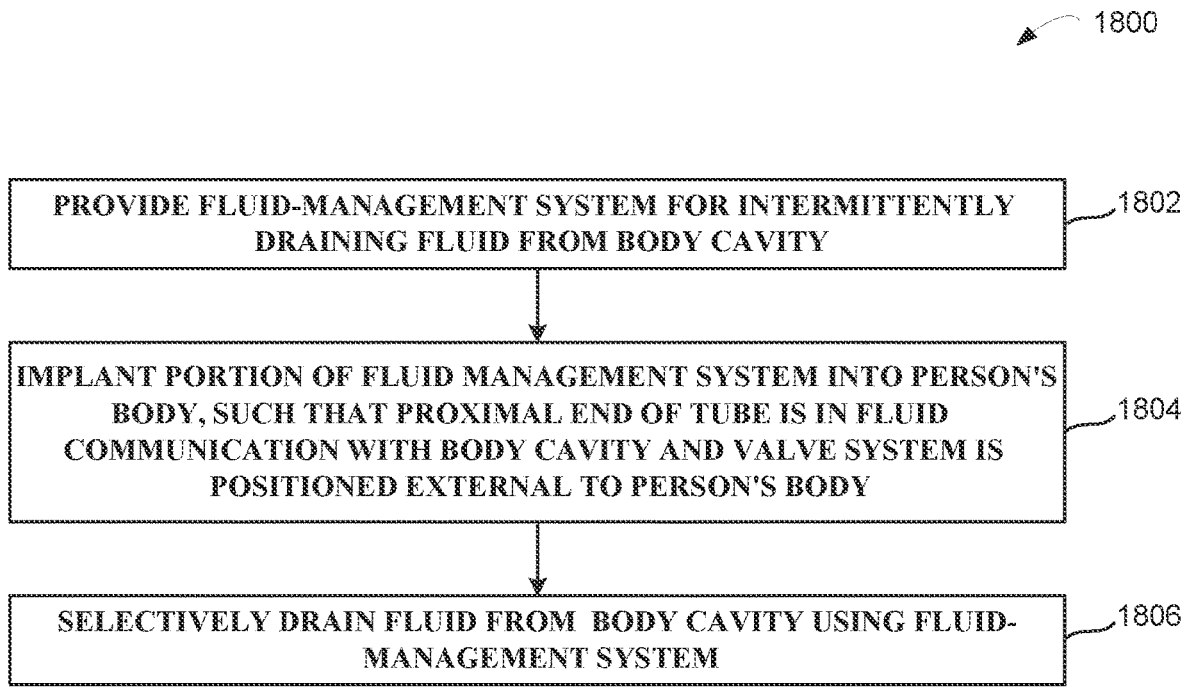
FIG. 18 shows an example method fluid management, according to an example of the present disclosure.

FIG. 18 shows a flowchart of an example method 1800 of fluid management. It should be understood that for this and other processes and methods disclosed herein, flowcharts show functionality and operation of one possible implementation of present embodiments. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

At block 1802, method 1800 involves providing a fluid-management system for selectively draining fluid from a body cavity. The fluid-management system comprises a valve assembly and a tube for carrying fluid from a body cavity of a person to the valve assembly, where the valve assembly is configured to be positioned external to the person's body and comprises (i) an inlet, (ii) an outlet, (iii) one or more one-way valves positioned between the inlet and outlet that are each configured to open and close based on fluctuations in pressure between a cavity of a person's body and the one-way valve, and (iv) an adjustable outlet lock configured to selectively prevent fluid movement through the outlet. At block 1804, method 1800 involves implanting a portion of the fluid-management system into the person's body, such that a proximal end of the tube is in fluid communication with the cavity and the valve assembly is positioned external to the person's body. At block 1806, after the fluid-management system is implanted into the person's body, the person may selectively drain fluid from the body cavity using the fluid-management system, as described above.

Figure 19:
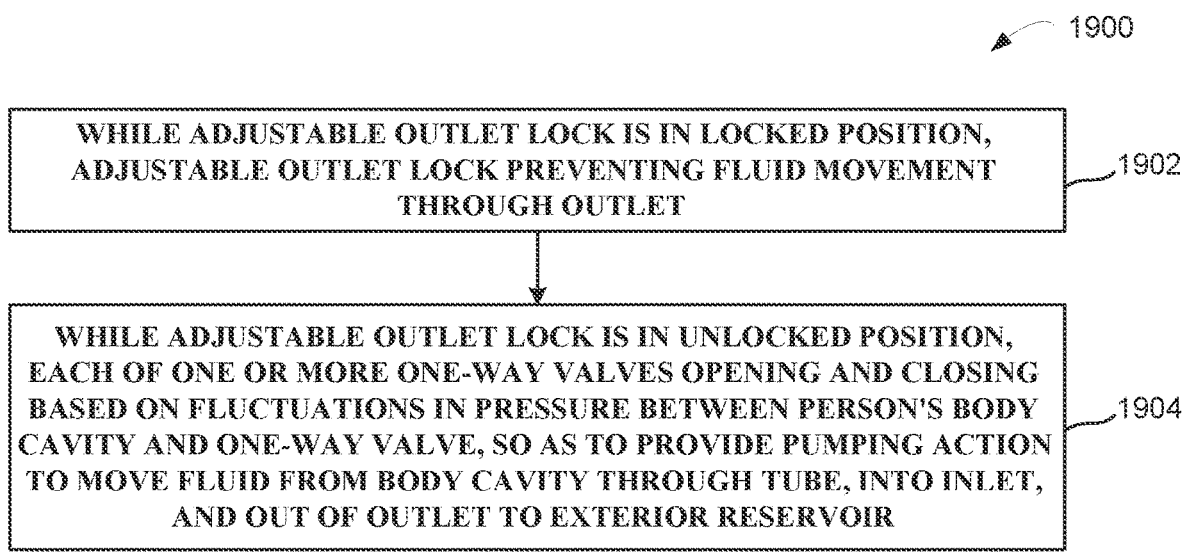
FIG. 19 shows an example method of draining fluid from a body cavity of a person to a reservoir external to the person's body, according to an example of the present disclosure.

FIG. 19 shows a flowchart of an example method 1900 of draining fluid from a body cavity of a person to a reservoir external to the person's body. In particular, method 1900 is a method of operation of a fluid-management system comprising a valve assembly and a tube for carrying fluid from a body cavity of a person to the valve assembly, where the valve assembly is configured to be positioned external to the person's body and comprises (i) an inlet, (ii) an outlet, (iii) one or more one-way valves positioned between the inlet and outlet that are each configured to open and close based on fluctuations in pressure between a cavity of a person's body and the one-way valve, and (iv) an adjustable outlet lock configured to selectively prevent fluid movement through the outlet. At block 1902, method 1900 involves while the adjustable outlet lock is in a locked position, the adjustable outlet lock preventing fluid movement through the outlet. At block 1904, method 1900 involves while the adjustable outlet lock is in an unlocked position, each of the one or more one-way valves opening and closing based on fluctuations in pressure between the person's body cavity and the one-way valve, so as to provide a pumping action to move fluid from the body cavity through the tube, into the inlet, and out of the outlet to an exterior reservoir. The fluctuations may occur based on respiratory action of a breathing cycle of the person.

Figure 20:
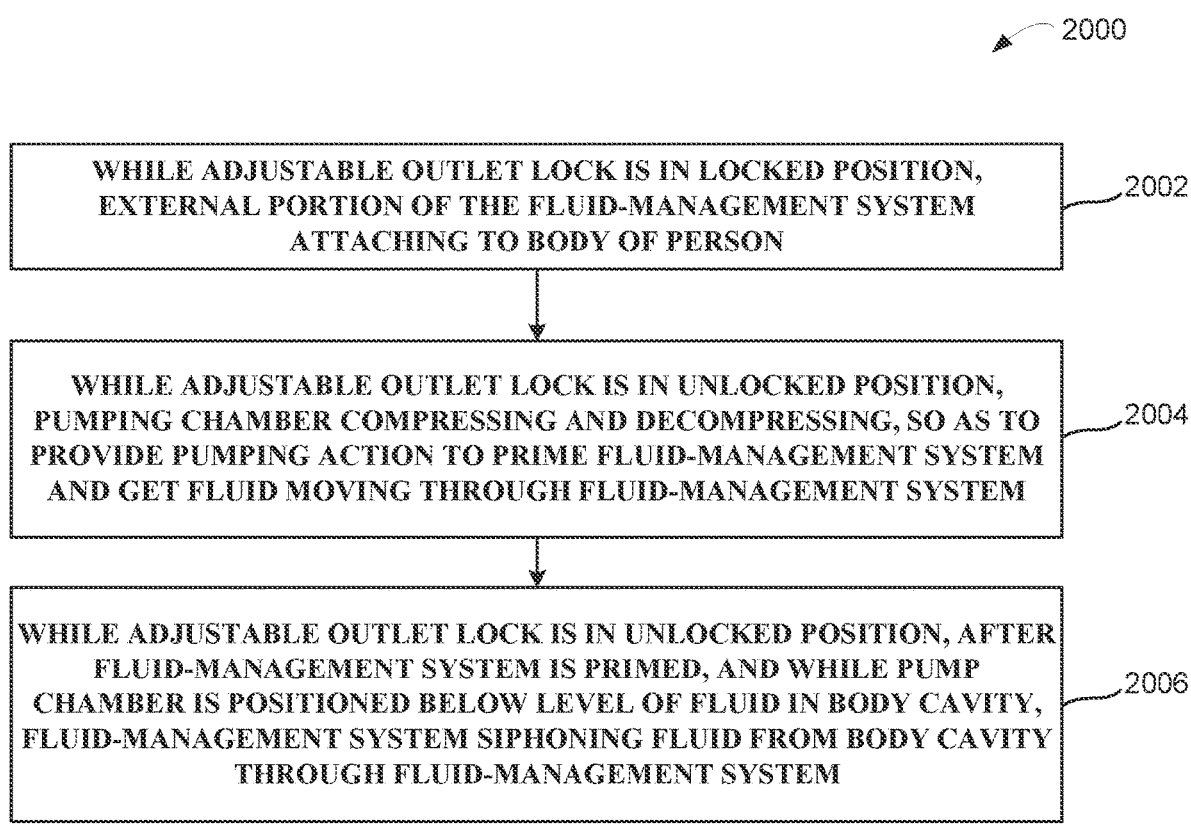
FIG. 20 shows an example method of draining fluid from a body cavity of a person to a reservoir external to the person's body, according to an example of the present disclosure.

FIG. 20 shows a flowchart of an example method 2000 of draining fluid from a body cavity of a person to a reservoir external to the person's body. In particular, method 2000 is a method of operation of a fluid-management system comprising a valve assembly and a tube for carrying fluid from a body cavity of a person to the valve assembly, wherein the valve assembly is positioned external to the person's body and comprises (i) an inlet, (ii) an outlet, (iii) a plurality of one-way valves positioned between the inlet and outlet and that are each configured to open and close based on fluctuations in pressure between the person's body cavity and the one-way valve, wherein the plurality of one-way valves are housed in a pumping chamber, and (iv) an adjustable outlet lock configured to selectively prevent fluid movement through the outlet.

At block 2002, method 2000 involves, while the adjustable outlet lock is in a locked position, an external portion of the fluid-management system attaching to a body of the person. In an example, the fluid-management system attaches to a chest wall of the person. At block 2004, method 2000 involves, while the adjustable outlet lock is in an unlocked position, the pumping chamber compressing and decompressing, so as to provide a pumping action to prime the fluid-management system and get fluid moving through the fluid-management system. Further, at block 2006, method 2000 involves, while the adjustable outlet lock is in the unlocked position, after the fluid-management system is primed, and while the pump chamber is positioned below a level of fluid in the body cavity, the fluid-management system siphoning fluid from the body cavity through the fluid-management system. The fluid may be drained to a reservoir external to the person's body. In an example, the pump chamber 402 is shown positioned below a level of fluid in the body cavity in FIG. 4B. However, in other examples, the tube may be longer and may be positioned further below the level of fluid in the body cavity.

Example embodiments of the disclosed innovations have been described above. Those skilled in the art will understand, however, that changes and modifications may be made to the embodiments described without departing from the true scope and spirit of the present invention, which will be defined by the claims. Further, to the extent that examples described herein involve operations performed or initiated by actors, such as "persons" or other entities, this is for purposes of example and explanation only. The claims should not be construed as requiring action by such actors unless explicitly recited in the claim language.

The invention claimed is:

1. A fluid-management system comprising:
   a valve assembly; and
   a tube for carrying fluid from a body cavity of a person to the valve assembly, wherein the valve assembly is configured to be positioned external to the person's body and comprises (i) an inlet, (ii) an outlet, (iii) a plurality of one-way valves positioned between the inlet and outlet, and (iv) an adjustable outlet lock positioned downstream of the plurality of one-way valves and configured to selectively prevent fluid movement through the outlet, and wherein the tube is configured to extend from the inlet of the valve assembly to the person's body cavity.

2. The fluid-management system of claim 1, wherein the valve assembly comprises a pumping chamber that houses the plurality of one-way valves, wherein the plurality of one-way valves comprise a first one-way valve positioned on a first side of the pumping chamber and a second one-way valve positioned on a second side of the pumping chamber, and wherein the pumping chamber is configured to be compressed and decompressed to pump fluid.

3. The fluid-management system of claim 2, wherein each one-way valve of the plurality of one-way valves is configured to open and close based on compression and decompression of the pumping chamber.

4. The fluid-management system of claim 3, wherein each one-way valve of the plurality of one-way valves is further configured to open and close based on fluctuations in pressure between the person's body cavity and the one-way valve that occur based on respiratory action of a breathing cycle of the person.

5. The fluid-management system of claim 4, wherein each one-way valve of the plurality of one-way valves is configured to (i) open due to positive pressure between the cavity and the one-way valve during an expiration phase of the breathing cycle and (ii) close due to negative pressure between the cavity and the one-way valve during an inspiration phase of the breathing cycle.

6. The fluid-management system of claim 1, wherein the valve assembly is non-removably attached to the tube, and wherein the adjustable outlet lock of the valve assembly is non-removably attached to the valve assembly.

7. The fluid-management system of claim 1, wherein the adjustable outlet lock is positioned at the outlet.

8. The fluid-management system of claim 1, wherein each one-way valve of the plurality of one-way valves is configured to open with a cracking pressure of less than about 25 cmH$_2$O.

9. The fluid-management system of claim 1, wherein the cracking pressure is less than about 5 cmH$_2$O.

10. The fluid-management system of claim 1, wherein each one-way valve of the plurality of one-way valves is configured to prevent retrograde flow.

11. The fluid-management system of claim 10, wherein each one-way valve of the plurality of one-way valves is configured to reseal with a differential back pressure of less than about 15 cmH$_2$O.

12. The fluid-management system of claim 11, wherein the differential back pressure is less than about 2 cmH$_2$O.

13. The fluid-management system of claim 1, wherein each one-way valve of the plurality of one-way valves comprises a plurality of lips defining a slit that is movable from a closed position to an open position, and wherein the lips are configured to have a surface area of interaction of less than 6 millimeters$^2$ when the slit is in the closed position.

14. The fluid-management system of claim 1, wherein the adjustable outlet lock is located at the outlet, and wherein the adjustable outlet lock is configured to move between a locked position in which the adjustable outlet lock seals the outlet and an unlocked position in which the adjustable outlet lock allows fluid movement through the outlet.

15. The fluid-management system of claim 14, wherein the adjustable outlet lock comprises at least one of a cap, a pinch lever, a twist pinch, or an offset device.

16. The fluid-management system of claim 1, wherein the valve assembly is non-removably attached to the tube.

17. The fluid-management system of claim 1, wherein the valve assembly comprises a body that houses the plurality of one-way valves, and wherein the body is coated with at least one of anticoagulation factors or fibrinolytic factors.

18. The fluid-management system of claim 1, wherein the cavity comprises one of a pleural cavity, a peritoneal cavity, a cerebrospinal cavity, a pericardial cavity, a breast cavity, or a cavity of a cystic lesion.

19. A method of operation of a fluid-management system comprising a valve assembly and a tube for carrying fluid from a body cavity of a person to the valve assembly, wherein the valve assembly is positioned external to the person's body and comprises (i) an inlet, (ii) an outlet, (iii) a plurality of one-way valves positioned between the inlet and outlet, wherein the plurality of one-way valves are housed in a pumping chamber, and (iv) an adjustable outlet lock positioned downstream of the plurality of one-way valves and configured to selectively prevent fluid movement through the outlet, the method comprising:
  while the adjustable outlet lock is in a locked position, an external portion of the fluid-management system attaching to a body of the person; and
  while the adjustable outlet lock is in an unlocked position, (i) the pumping chamber compressing and decompressing, so as to provide a pumping action to prime the fluid-management system and get fluid moving through the fluid-management system and (ii) after the fluid-management system is primed and while the pump chamber is positioned below a level of fluid in the body cavity, the fluid-management system siphoning fluid from the body cavity through the fluid-management system.

* * * * *